(12) United States Patent
Zeng et al.

(10) Patent No.: US 9,687,152 B2
(45) Date of Patent: Jun. 27, 2017

(54) APPARATUS AND METHODS FOR MULTIPHOTON MICROSCOPY

(75) Inventors: Haishan Zeng, Vancouver (CA); Harvey Lui, Vancouver (CA); David McLean, Vancouver (CA); Anthony Lee, Vancouver (CA); Hequn Wang, Vancouver (CA); Shuo Tang, Vancouver (CA)

(73) Assignee: Britisg Columbia Cancer Agency Branch, Vancouver (CA)

( * ) Notice: Subject to any disclaimer, the term of this patent is extended or adjusted under 35 U.S.C. 154(b) by 708 days.

(21) Appl. No.: 14/009,473

(22) PCT Filed: Apr. 5, 2012

(86) PCT No.: PCT/CA2012/050223
§ 371 (c)(1),
(2), (4) Date: Oct. 2, 2013

(87) PCT Pub. No.: WO2012/135961
PCT Pub. Date: Oct. 11, 2012

(65) Prior Publication Data
US 2014/0023993 A1 Jan. 23, 2014

Related U.S. Application Data

(60) Provisional application No. 61/473,267, filed on Apr. 8, 2011.

(51) Int. Cl.
*A61B 5/00* (2006.01)
*A61B 5/06* (2006.01)
(Continued)

(52) U.S. Cl.
CPC .......... *A61B 5/0064* (2013.01); *A61B 5/0071* (2013.01); *A61B 5/0075* (2013.01);
(Continued)

(58) Field of Classification Search
None
See application file for complete search history.

(56) References Cited

U.S. PATENT DOCUMENTS 5,034,613 A * 7/1991 Denk .................. G01N 21/6402
250/458.1
5,149,972 A * 9/1992 Fay .................... G01N 21/6458
250/372

(Continued)

*Primary Examiner* — Andy Rao
*Assistant Examiner* — Tyler Edwards
(74) *Attorney, Agent, or Firm* — Oyen Wiggs Green & Mutala LLP

(57) ABSTRACT

A multiphoton microscope is provided. The microscope includes: an excitation source for providing an optical excitation beam at an excitation wavelength $\lambda$; a scanner for scanning the excitation beam on a sample; an objective for irradiating the sample with the excitation beam scanned by the scanner and for collecting an emission beam from the sample; a first detector for detecting a plurality of multiphoton signals; and an emission light path allowing transmission from the objective to the first detector a wavelength band limited to greater than or equal to $\lambda/2$ and less than $\lambda$, wherein the plurality of multiphoton signals have wavelengths within the wavelength band; wherein the plurality of multiphoton signals com-prises a first multiphoton signal and a second multiphoton signal of different types. Fast image capture rate multiphoton microscopes for in vivo imaging, as well as photothermolysis methods using the microscopes are also provided.

44 Claims, 39 Drawing Sheets

(51) Int. Cl.
  *G02B 21/00*   (2006.01)
  *G02B 21/06*   (2006.01)
  *G01J 3/44*    (2006.01)
  *G01J 3/02*    (2006.01)
  *A61B 18/18*   (2006.01)
  *A61N 5/06*    (2006.01)

(52) U.S. Cl.
  CPC .......... *A61B 5/4836* (2013.01); *A61B 5/6831* (2013.01); *A61B 5/6832* (2013.01); *A61B 18/18* (2013.01); *A61N 5/06* (2013.01); *G01J 3/027* (2013.01); *G01J 3/0218* (2013.01); *G01J 3/44* (2013.01); *G02B 21/0052* (2013.01); *G02B 21/0076* (2013.01); *G02B 21/06* (2013.01); *A61N 5/0616* (2013.01)

(56) References Cited

U.S. PATENT DOCUMENTS

| | | | |
|---|---|---|---|
| 5,885,211 A * | 3/1999 | Eppstein | A61B 5/14514 600/309 |
| 2003/0148393 A1 | 8/2003 | Woodbury et al. | |
| 2005/0259249 A1 | 11/2005 | Dombeck et al. | |
| 2007/0057211 A1 * | 3/2007 | Bahlman | G01N 21/6452 250/584 |
| 2007/0229801 A1 * | 10/2007 | Tearney | A61B 5/0062 356/73 |
| 2008/0205833 A1 * | 8/2008 | Fu | A61B 1/00096 385/117 |
| 2010/0259605 A1 | 10/2010 | So et al. | |
| 2010/0284024 A1 | 11/2010 | Vucinic et al. | |
| 2012/0029490 A1 * | 2/2012 | Lin | A61F 9/008 606/4 |

* cited by examiner

Figure 33A                    Figure 33B

APPARATUS AND METHODS FOR MULTIPHOTON MICROSCOPY

REFERENCE TO RELATED APPLICATIONS

This application claims priority from U.S. provisional patent application No. 61/473,267 filed 8 Apr. 2011 entitled APPARATUS FOR COMPLEX MICRO-SPECTROSCOPY AND CONFOCAL MULTIPHOTON MICROSCOPY VIDEO IMAGING SYSTEM. For purposes of the United States, this application claims the benefit under 35 U.S.C. §119 of U.S. provisional patent application No. 61/473,267 filed 8 Apr. 2011, which is hereby incorporated herein by reference for all purposes.

TECHNICAL FIELD

This invention relates to apparatus and methods for multiphoton microscopy. The invention may for example be used in in vivo diagnosis and treatment of skin diseases.

BACKGROUND

Non-invasive diagnostic imaging techniques for examining the microscopic structure of tissue is desirable for the skin, where the standard examination practice of biopsy can lead to scarring. Two techniques that have garnered much interest in recent years for dermatology use are reflectance confocal microscopy (RCM) and multiphoton microscopy (MPM). The optical sectioning capability of RCM allows in vivo, high resolution morphological images of skin. MPM also has inherent optical sectioning capabilities and allows sensitive in vivo imaging at great depths.

Multiphoton signals include signals from multiphoton fluorescence and sum frequency generation. Multiphoton fluorescence occurs when two or more photons of relatively lower energy are simultaneously absorbed by and excite a fluorophore, causing emission of a fluorescence photon at a higher energy than the excitation photons. Sum frequency generation occurs when two or more photons interact with a nonlinear material and combine to form a new photon with a multiple of the frequency and a fraction of the wavelength of the initial photons. Both multiphoton fluorescence and sum frequency generation is localized to where the light source, for example a femtosecond laser, is focused and provides a high flux of photons.

Different MPM excitation mechanisms are sensitive to different biochemical compositions of the tissue. For example, two-photon fluorescence (TPF) signals arise from endogenous fluorophores of skin components such as elastin, NAD(P)H, and keratin; while second harmonic generation (SHG) is sensitive to non-centrosymmetric structures such as collagen.

As there is less scattering and absorption of the near infrared light used in MPM, there is deeper penetration as well as less photo-damage to the tissue. Combining both RCM and MPM imaging (RCM/MPM imaging) potentially allows greater clinical diagnostic utility as complementary information can be revealed using the two techniques. RCM/MPM imaging has been applied in ex vivo and in vivo studies. For clinical application, in vivo imaging is preferred over ex vivo imaging because it does not necessitate tissue removal. It also leaves the tissue in its native state, whereas ex vivo tissue can be subject to biochemical/structural changes due to the degradation of the sample, tissue contraction, and elimination of living tissue dynamics such as blood perfusion and oxygenation.

In vivo skin imaging is complicated because patient motion must be mitigated, and often multiple or large lesions must be examined. Some in vivo MPM systems have imaging rates varying from 1 s to 24 s per frame for titanium sapphire laser systems based at 800 nm, and 0.5 s to 2 s per frame for chromium-forsterite laser systems based around 1250 nm. These slow imaging rates can result in blurred images and prolonged imaging times. Fast imaging rate is important for decreasing blurring effects and reducing patient imaging times.

Conventional MPM systems with multiple imaging modes typically employ a dedicated photomultiplier tube (PMT) for each imaging modality. For example, MPM systems that detect both TPF and SHG signals use a dichroic mirror to separate light emitted from the sample into the two signals and direct the signals to respective PMTs. Filters are also typically located in the emitted light path before each PMT. Optical components such as mirrors and filters decrease signal strength by absorbing and/or reflecting some of the emitted light and also by causing the emitted light path to be longer in order to accommodate placement of the optical components. A further disadvantage is that changing wavelengths to switch between multiphoton imaging modes requires changing out or adjusting these optical components, increasing the complexity of the system as well as increasing the time and labour associated with imaging in multiple modes.

Selective photothermolysis is based on the selective absorption of pulsed light radiation by the targeted chromophores. In selective photothermolysis based skin phototherapy, for example, the therapeutic laser simultaneously illuminates a large volume of tissue. For successful therapy, heat generation must be restricted to the targeted chromophores only, which is done by selecting a laser wavelength at which the targeted chromophores have much higher light absorption than non-targeted components. This type of skin phototherapy has been somewhat successful in treating pigmented skin diseases and in permanent hair removal. However, side effects and inefficiencies occur when there is less selectivity of light absorption by the target chromophores.

Apparatus and methods of multiphoton microscopy that address one or more disadvantages of conventional systems are desirable.

SUMMARY

The following embodiments and aspects thereof are described and illustrated in conjunction with systems, tools and methods which are meant to be exemplary and illustrative, not limiting in scope. In various embodiments, one or more of the above-described problems have been reduced or eliminated, while other embodiments are directed to other improvements.

One aspect of the invention relates to a microscope having (a) excitation source for providing an optical excitation beam at an excitation wavelength $\lambda$; (b) a scanner for scanning the excitation beam on a sample; (c) an objective for irradiating the sample with the excitation beam scanned by the scanner and for collecting an emission beam from the sample; (d) a first detector for detecting a plurality of multiphoton signals; and (e) an emission light path allowing transmission from the objective to the first detector a wavelength band limited to greater than or equal to $\lambda/2$ and less than $\lambda$, wherein the plurality of multiphoton signals have wavelengths within the wavelength band; wherein the plurality of multiphoton signals comprises a first multiphoton signal and a second multiphoton signal of different types. Another aspect of the invention relates to a microscope for in vivo imaging of a subject, the microscope including: an excitation source for providing an optical excitation beam; a scanner for scanning the excitation beam on a target region of the subject, wherein the scanner comprises a resonant scanner; an objective for irradiating the target region with the excitation beam scanned by the scanner and for collecting an emission beam from the target region; a detector for detecting a plurality of multiphoton signals from the emission beam; an adapter comprising a surface for detachably securing to an area around the target region; a translation stage comprising a table and a base, the table movably coupled to the base, wherein the objective is mounted to the table and the base is coupled to the adapter.

A further aspect of the invention relates to a photothermolysis method including the steps of:
  (a) visualizing a target structure using a microscope according to the invention;
  (b) tuning an excitation light source of the assembly to a wavelength at which multiphoton absorption will occur within the target structure;
  (c) increasing power output of the excitation light source to cause heat to be generated within the target structure.

In addition to the exemplary aspects and embodiments described above, further aspects and embodiments will become apparent by reference to the drawings and by study of the following detailed descriptions.

BRIEF DESCRIPTION OF THE DRAWINGS

Exemplary embodiments are illustrated in referenced figures of the drawings. It is intended that the embodiments and figures disclosed herein are to be considered illustrative rather than restrictive.

In drawings which illustrate non-limiting embodiments of the invention:

FIG. 33A is an image of normal skin taken using a multiphoton microscopy assembly according to an embodiment of the invention, FIG. 33B is an H&E stained sample of same.

DESCRIPTION

Throughout the following description, specific details are set forth in order to provide a more thorough understanding of the invention. However, the invention may be practiced without these particulars. In other instances, well known elements have not been shown or described in detail to avoid unnecessarily obscuring the invention. Accordingly, the specification and drawings are to be regarded in an illustrative, rather than a restrictive sense Some embodiments of the invention relate to apparatus and methods for multiphoton microscopy of microstructures. Some embodiments of the invention relate to apparatus and methods for multiphoton microscopy of biological samples in vivo. Some embodiments of the invention relate to apparatus and methods for real time imaging of biological samples in vivo. Some embodiments of the invention relate to apparatus and methods for diagnosis and/or treatment of biological conditions such as skin conditions. Integrated detection of a plurality of multiphoton signals by a single detector at different wavelengths provides improved imaging sensitivity and operator convenience compared to conventional systems. Multiphoton signals may include second harmonic generation (SHG) and two-photon fluorescence (TPF) signals, for example.

Multiphoton Microscopy Assemblies

Figure 1:
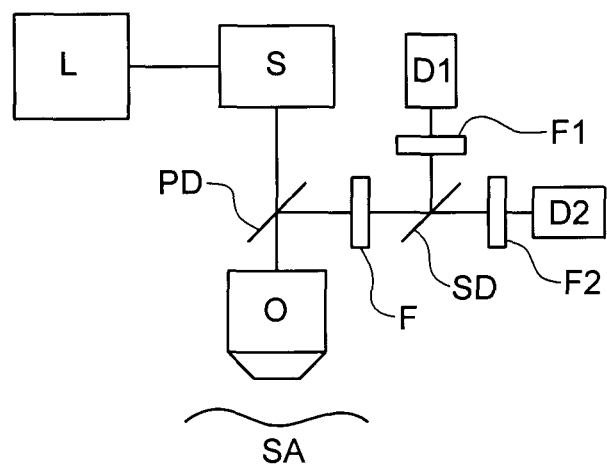
FIG. 1 is a schematic of a known multiphoton microscopy assembly.

FIG. 1 is a schematic illustration of a general layout of a known multiphoton microscopy assembly. Laser L directs excitation light to scanner S for scanning through an objective O onto a sample SA. Multiphoton signals emitted from sample SA are reflected by primary dichroic PD through a filter F to a secondary dichroic SD. Secondary dichroic SD splits the signals into TPF and SHG signals for passing through respective filters F1 and F2 for detection by respective detectors D1 and D2. Secondary dichroic SD and filters F1 and F2 are selected depending on the wavelength of the excitation light.

Figure 2A:
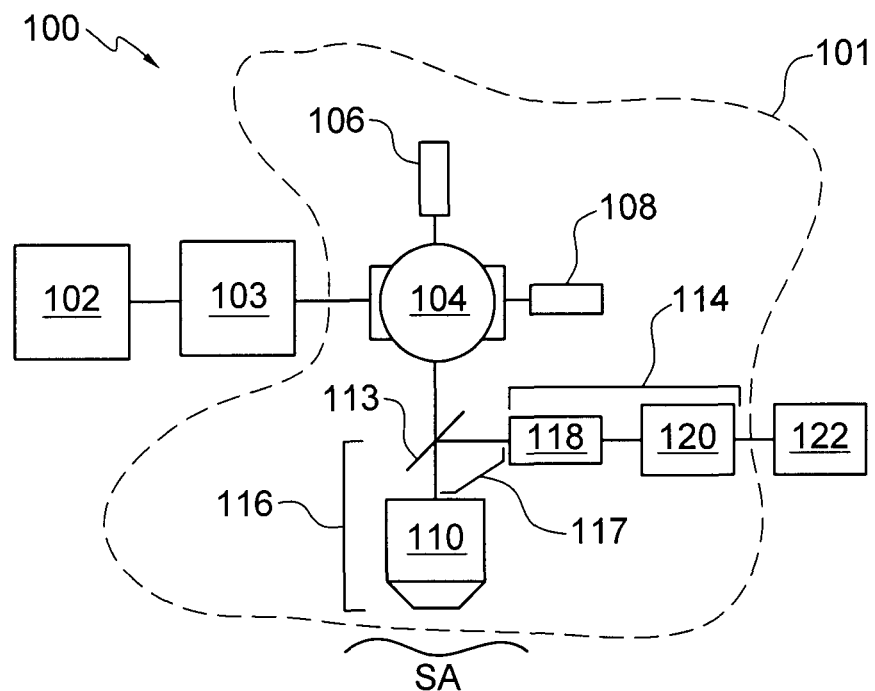
FIG. 2A is a schematic of a multiphoton microscopy assembly according to an embodiment of the invention.

FIG. 2A shows a multiphoton microscopy assembly 100 according to an example embodiment of the invention. Assembly 100 has an excitation light source 102. Excitation light source may be a laser. The laser may be collimated. The laser may be tunable, for example from 720 nm-950 nm. The laser may be a femtosecond laser. The pulse frequency of the femtosecond laser may for example be 80 MHz.

The power of the excitation light from excitation light source 102 is attenuated by attenuator 103. Attenuator 103 may be positioned near the output aperture of excitation light source 102. In some embodiments, attenuator 103 comprises a half wave plate and a polarizing beam splitter.

Scanner 104 scans the attenuated excitation light from attenuator 103. In some embodiments, scanner 104 comprises a resonant scanner 106 scanning for the fast axis (x-axis). In some embodiments, scanner 104 comprises a galvanometer scanner 108 for the slow axis (y-axis). Resonant scanner 106 may for example scan at a fixed scanning frequency. In some embodiments, the fixed scanning frequency may be about 8 kHz. In example embodiments scanner 104 may realize a scanning rate of 12 frames per second for a 512×512 pixel frame size. This scanning rate is suitable for real-time in vivo imaging. In some embodiments the scanning rate is at least several Hertz. For example the scanning rate may be 10 Hz or greater.

Scanned excitation light from scanner 104 is directed to the back aperture of objective 110. Objective 110 may be an immersion objective. The magnification of objective 110 may for example be in the range of 20× to 100×. In certain embodiments the magnification of objective 110 is 60×. The numerical aperture (NA) of objective 110 may for example be in the range of 0.45 to 1.2. In certain embodiments the NA of objective 110 is 1.0. Adjusting the amplitudes of resonant scanner 106 and galvanometer scanner 108 may permit a variable field of view. The variable field of view may for example range from 10 μm×10 μm to 500 μm×500 μm. Objective 110 focuses the scanned excitation light to a focus location lying in a region of interest in sample SA.

Multiphoton signals emitted from sample SA are reflected by wavelength selector 113, which may comprise a primary dichroic, directly onto a single detector 118 on detection arm 114. Detector 118 detects a plurality of multiphoton signals such as multiphoton fluorescence (e.g. two photon fluorescence (TPF), three photon fluorescence) and sum frequency generation (e.g. second harmonic generation (SHG), third harmonic generation).

Detection of a plurality of types of multiphoton signals (e.g. multiphoton fluorescence signals and sum frequency generation signals) by one detector 118 obviates the need for a secondary dichroic and the need for the filters between the secondary dichroic and the detectors. The absence of these intermediate optical components between objective 110 and detector 118 provide increased signal sensitivity due to less transmission and reflection losses by intermediate optical components and a shortened emitted light path compared to conventional systems. The absence of these intermediate optical components also obviates the need to change or adjust such components as excitation wavelength is varied. The absence of these intermediate optical components also allows the operator to optimize the excitation wavelength, and therefore the strength of a particular multiphoton signal, in real time without interruption. In some embodiments, particularly for clinical applications, assembly 100 comprises a user interface configured to allow an operator to select from a plurality of endogenous fluorophores to view in real time, additionally or alternatively to selecting or varying the excitation wavelength.

In some embodiments, emission light path 117 from objective 110 to detector 118 passes a wavelength band that comprising a plurality of multiphoton signals to be detected by detector 118. For example, for detection of TPF and SHG, emission light path 117 permits passage of TPF signals having wavelengths greater than $\lambda/2$ but less than $\lambda$ and SHG signals having a wavelength equal to $\lambda/2$, where $\lambda$ is the excitation wavelength. In other words, for integrated detection of TPF and SHG signals, emission light path 117 permits passage of a wavelength band comprising wavelengths that are equal to or greater than $\lambda/2$ but less than $\lambda$. This restriction to a desired wavelength band along emitted light path 117 may be accomplished by a wavelength selector 113. Wavelength selector 113 may direct signals having wavelengths equal to or greater than $\lambda/2$ but less than $\lambda$ to detector 118. Wavelength selector 113 may direct signals outside of the desired wavelength band elsewhere or absorb them.

In some embodiments, wavelength selector 113 may comprise a dichroic and a shortpass filter. The dichroic may for example be a 665 nm dichroic mirror (e.g. SemRock FF665-D, 02-25X36) in embodiments where TPF and SHG signals are being detected by detector 118. The dichroic mirror may, for example, have a greater than 90% transmittance in the 680 to 1600 nm range (i.e., transmits all excitation wavelengths, e.g. 720-950 nm), and greater than 90% reflectance in the 350 to 650 nm range. The shortpass filter ensures only signals having a wavelength less than that of the excitation wavelength is transmitted.

In other embodiments, for detection of three photon fluorescence (3PF) and third harmonic generation (THG), emission light path 117 may permit passage of 3PF signals having wavelengths greater than $\lambda/3$ but less than $\lambda$ and THG signals having a wavelength equal to $\lambda/3$, where $\lambda$ is the excitation wavelength. In other words, emission light path 117 may, for example by way of a wavelength selector 113, permit passage of a wavelength band comprising wavelengths that are equal to or greater than $\lambda/3$ but less than $\lambda$. In such embodiments, wavelength selector 113 may comprise a dichroic having greater than 90% transmittance in the 680 to 1600 nm range (i.e., transmits all excitation wavelengths, e.g. 720-950 nm), and greater than 90% reflectance in the 240 to 650 nm range. The shortpass filter ensures only signals having a wavelength less than that of the excitation wavelength are transmitted.

Detector 118 may for example comprise a high-UV/visible-sensitivity photomultiplier tube (PMT). In some embodiments the PMT is operated in analog mode (instead of photon counting mode) for a fast response.

Figure 2B:
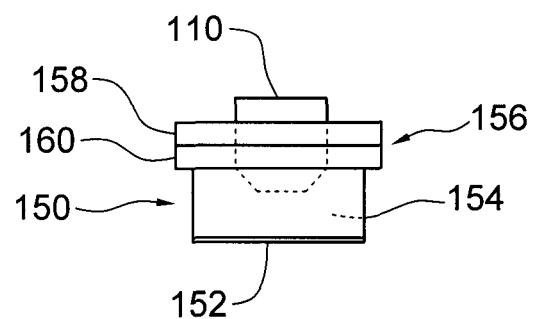
FIG. 2B is a side view of an adapter of the multiphoton microscopy assembly of FIG. 2A.

FIG. 2B shows an adapter 150 according to an example embodiment of the invention. Adapter 150 stabilizes the region of interest on the subject's body with respect to an objective such as objective 110 of assembly 100. Illustrated adapter 150 is a hollow cylinder. In other embodiments adapter 150 may be any other suitable shape. Adapter 150 may be formed from a rigid material. In some embodiments, the perimeter of an open end of adapter 150 defines an attachment surface 152 for detachably securing adapter 150 to the region of interest on the subject's body. Attachment surface 152 may for example comprise a non-permanent adhesive. In some embodiments, the end of adapter 150 that detachably secures to the subject's body comprises a transparent window instead of an opening. In some embodiments, adapter 150 may be provided with straps or the like that wrap around the immediate body part (e.g. around the forearm, leg, torso, etc.) for detachably securing attachment surface 152 against the subject's skin. Adapter 150 has an interior 154 for containing an objective immersion medium such as oil, water, glycerin or the like.

A translation stage 156 comprising a plate 158 movably coupled to a base 160. Translation stage 156 may be manually operated or motorized, for example. Base 160 is fixed to adapter 150. In some embodiments, base 160 and adapter 150 may be integrally formed. Plate 158 may move in the XY or XYZ directions in relation to base 160. In embodiments where plate 158 moves in the XY directions, objective 110 may be a focusing objective. An objective 110 of assembly 100, is securely mounted to plate 158. In some embodiments, objective portion 116 and detection portion 114 are disposed on the end of a cantilevered arm (not shown) extending out from an optical table (not shown) or other suitable vibration isolating support. The optical table may support other components of assembly 100 such as light source 102 and scanner 104. The cantilevered arm may be moveable to facilitate positioning of objective portion 116.

In some embodiments, at least part of assembly 100 may be housed in a handheld probe to facilitate clinical use. For example, the components bounded by the stippled area 101 in FIG. 2A may be miniaturized and housed in a handheld probe. In some embodiments, light is delivered from attenuator 103 to scanner 104 through an optical fiber, such as a photonic crystal fiber (PCF). A focus lens may be provided between attenuator 103 and the PCF to focus light into the PCF. A further lens may be provided after the PCF to collimate the light beam before the light enters scanner 104. In some embodiments, providing such an optical fiber facilitates separately and conveniently housing the components such as those bounded by the stippled area 101 in a handheld probe.

An amplifier 120 amplifies signals received from detector 118 prior to input into and recordal by a frame grabber 122. Frame grabber 122 may for example be a 10-bit multichannel frame grabber.

As resonant scanner 106 scans bidirectionally, the forward and backward passes of each fast axis line were added during post-processing.

Figure 3:
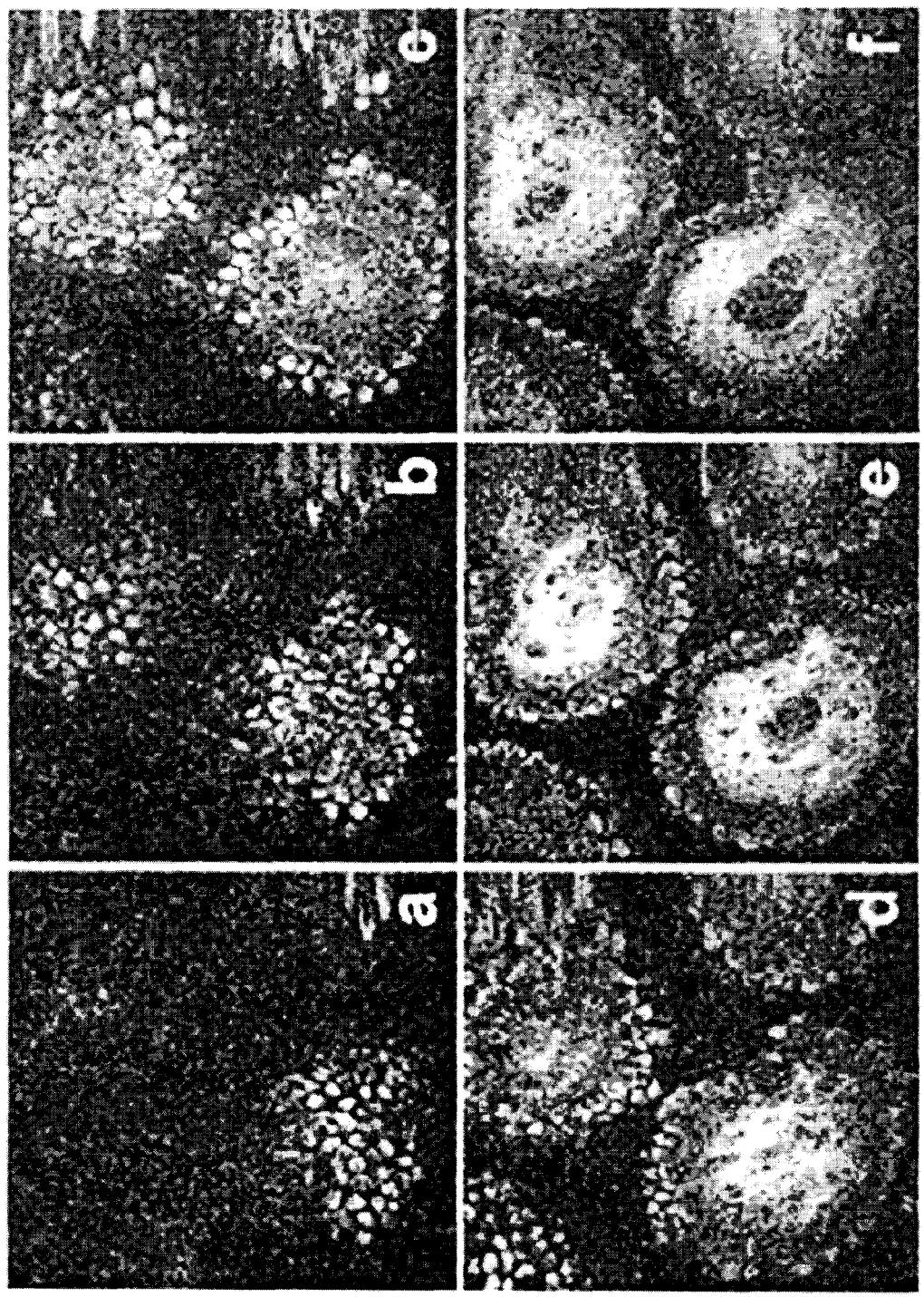
FIG. 3(a) to (f) are images of human skin taken using the multiphoton microscopy assembly of FIG. 2A.
Figure 4:
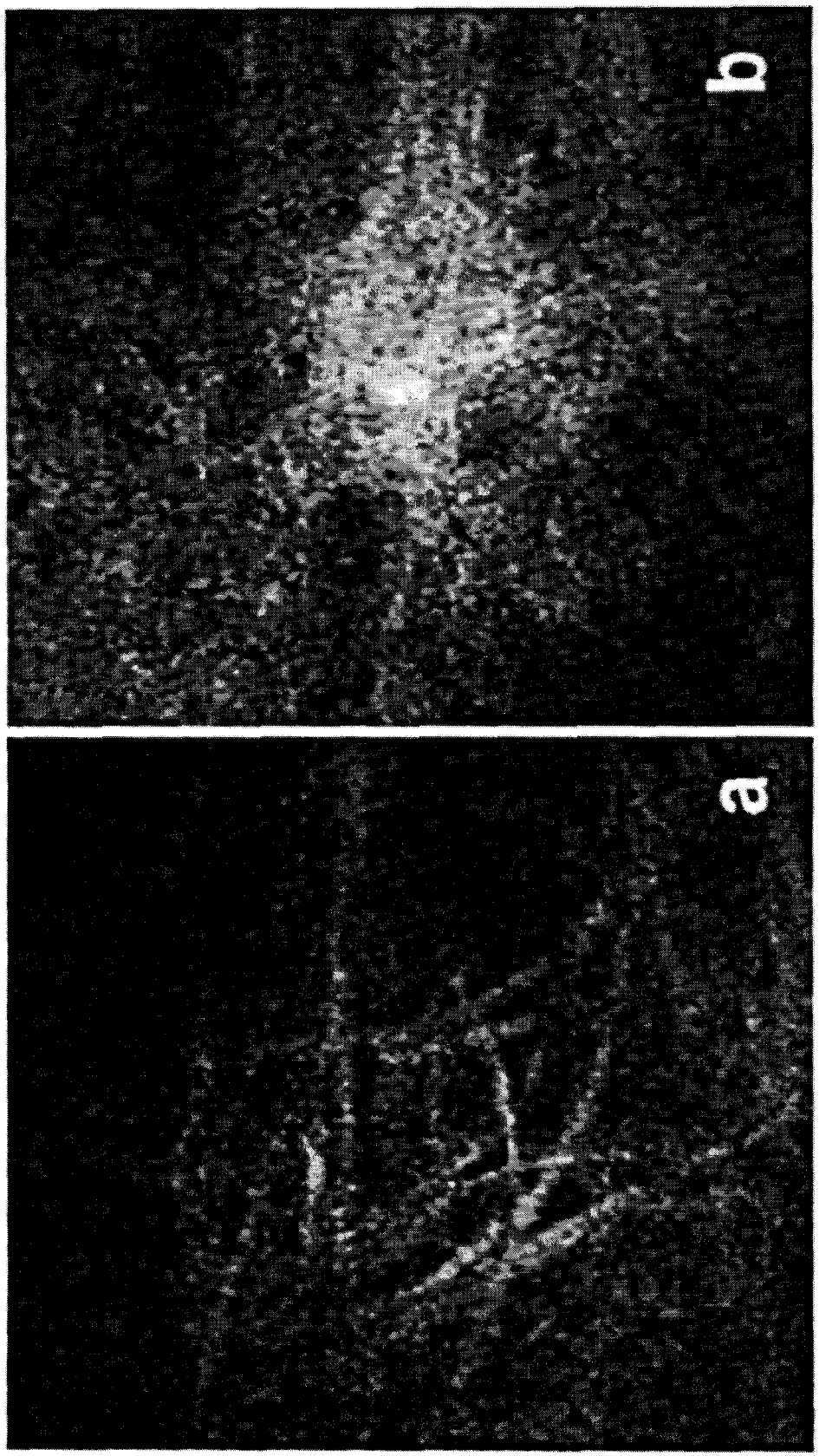
FIG. 4(a) to (b) are images of human skin taken using a multiphoton microscopy assembly according to an embodiment of the invention.

FIG. 3 shows combined TPF and SHG images extracted from an in vivo video obtained with a prototype multiphoton microscopy assembly 100 having the structure shown in FIG. 2A. FIG. 4 shows overlayed TPF and SHG images extracted from in vivo videos obtained with a multiphoton microscopy assembly similar to assembly 100 but with a secondary dichroic and respective filters to separate and direct the TPF and SHG signals to individual detectors rather than a single combined detector as in assembly 100.

The images shown in FIGS. 3 and 4 show some distortion near the left and right edges because they have not been corrected for the sinusoidal scan pattern of the resonant scanner. Distortion on the left side of the images may be mitigated by delaying the start of line acquisition relative to the resonant scanner turning point on the left side. To obtain the imaging quality shown in FIGS. 3 and 4 acquired images were rebinned by a factor of 2 resulting in a frame size of 256×256 pixels. Image acquisition time for the images shown in FIGS. 3 and 4 was 1/15 s.

For imaging experiments, a steel ring was fixed to the dorsal forearms of volunteers using a double-sided adhesive film. No film or coverslip was present between the objective and the skin surface. Water was placed within the ring prior to mating with a magnetic holder. The magnetic holder was mounted to a manually actuated 3-dimensional translation stage to control imaging location and depth. An objective was mounted to the stage. Excitation light was attenuated to less than or equal to 40 mW. A shutter was used to block the laser when images were not being acquired.

FIG. 3(a) to (f) are images of the skin of a Caucasian male volunteer acquired using the single detector setup of assembly 100 at an excitation wavelength of 900 nm. The images are of the epidermal ridges and the papillary layer of the dermis, with imaging depth increasing from FIG. 3(a) to (f) starting from the dermal/epidermal boundary. The field of view is 200 µm×200 µm. The papillary structure at the epidermal/dermal boundary is clearly evident. Although cells in the upper epidermis are not visualized at this wavelength, the basal cells show up quite clearly as does the fibrous layer in the dermis that lies below the epidermal/dermal boundary. Interestingly, the fibrous layer consisting of collagen and/or elastin only provides a multiphoton signal in a thin layer immediately below the epidermal/dermal boundary (e.g. the fibrous structures are shown as rings in FIG. 3 (e) and (f)) even though the dermis consists mainly of these two components. This suggests that imaging at this wavelength is sensitive only to a particular type of collagen or elastin present in this thin layer.

FIGS. 4(a) and (b) are overlayed TPF and SHG images of the skin of a male volunteer acquired using a multiple detector set up at 880 nm excitation. The field of view is 200 µm×200 µm. The images collected from the reticular dermis clearly show elastin fiber bundles in the TPF channel and collagen fiber bundles in the SHG channel. A 458 nm secondary dichroic mirror was used to separate the SHG and TPF signals. 440/40 nm bandpass and 458 longpass filters were placed in front of the SHG and TPF detectors respectively. The SHG/TPF dichroic and filters preceding the detectors were changed according to the excitation wavelength used.

The frame capture rate for the videos from which the images in FIGS. 3 and 4 are derived was ~12 fps. This rate was limited by the particular resonant scanner, image resolution, and frame grabber employed. Faster frame capture rates are possible with other combinations of the foregoing. The same embodiment used for FIGS. 3 and 4 achieved ~27 fps frame capture rate with lower image resolution (256×256 pixels). In some embodiments, a higher frequency resonant scanner (e.g. 16 kHz) can be used to obtain frame capture rates of ~30 fps with image resolution of 512×512 pixels.

Clearly evident in the videos from which FIGS. 3 and 4 were derived were the frame to frame jumps in the z-imaging plane due to patient motion, underlining the need for fast imaging frame rates. Even when patient motion was reduced to a minimum, cardiac pulsation was seen in some instances. Imaging at a slower frame rate could result in significant blurring of the image.

Figure 5A:
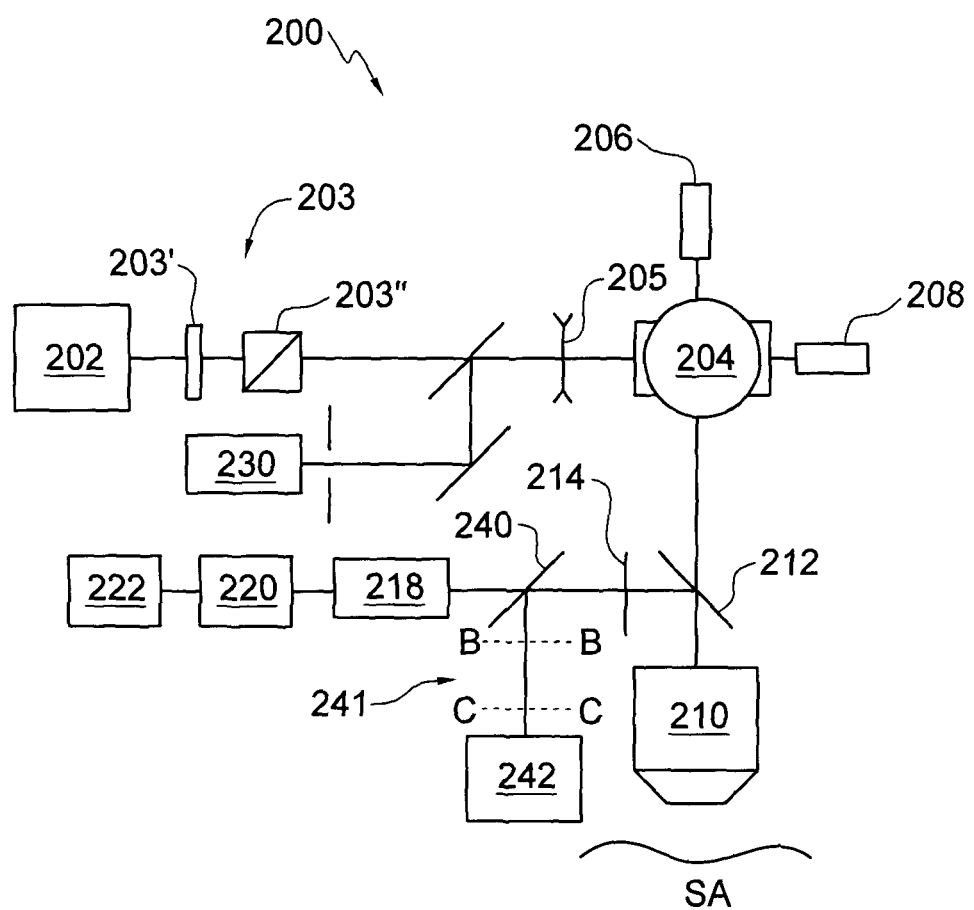
FIG. 5A is a schematic of a multiphoton microscopy assembly according to an embodiment of the invention.

FIG. 5A shows a multiphoton microscopy assembly 200 according to an example embodiment of the invention. Assembly 200 is similar to assembly 100 but is configurable to provide a confocal reflectance microscopy (RCM) imaging mode and a spectroscopy mode.

Excitation light power from an excitation light source 202 is attenuated by an attenuator 203 which includes half wave plate 203' and polarization beam splitter (PBS) 203". In some embodiments, attenuator 203 is installed directly at the output aperture of light source 202. Rotation of half wave plate 203' will change the polarization of light. In other embodiments the polarization of light may be changed by other known means. PBS 203" attenuates excitation light power at a variable ratio according to the polarization of the light. Excitation power applied on the sample SA is therefore adjustable by controlling the rotation angle of half wave plate 203'. In some embodiments a computer-controlled motor (not shown) is coupled to rotate half wave plate 203'. The computer-controlled motor may thereby automatically adjust excitation power. The power may for example be reduced to be less than ~200 mW by half wave plate 203' and polarization beam splitter 203" in order to result in a power level of around 30 mW at the sample SA after accounting for transmission and reflection loss due to other optical components in the light path.

Excitation light may be expanded by a beam expander 205, for example after attenuation by attenuator 203.

Attenuated excitation light may be scanned by a scanner 204. In an example embodiment, scanner 204 comprises a resonant scanner 206 scanning for the fast axis (x-axis), and a galvanometer scanner 208 for the slow axis (y-axis). In other example embodiments, resonant scanners may scan both fast and slow axes. In yet other example embodiments, galvanometer scanners may scan both fast and slow axes, although this would result in slower frame capture rates due to the slower scanning speed. Scanned light is focused on sample SA by objective 210.

Emitted light from sample SA passes through objective 210 and is divided by primary dichroic 212 into two beams. A first beam is transmitted through dichroic 212, is descanned by scanner 204, is directed by mirrors through a pin hole, and collected by detector 230 for RCM imaging. A second beam is reflected by a wavelength separator comprising a dichroic mirror 212 and shortpass filter 214, and separated by beam splitter 240 into another two beams, one collected by spectrometer 242 and the other transmitted to a single detector 218 for detecting multiphoton signals. Since both the confocal reflectance imaging and multiphoton imaging share the same excitation light source, scanner, and objective, the resulting multiphoton images and RCM images are automatically co-registered.

The emitted light beam directed to spectrometer 242 is coupled into a fibre bundle 241 by a fibre coupler lens, transmitted through fibre bundle 241, and collected by the spectrometer 242.

In some embodiments, spectrometer 242 is a Raman spectrometer. Excitation light source 202 may comprise an external cavity stabilized diode laser. The laser may produce an excitation light with a wavelength of 785 nm. Spectrometer 242 may comprise a transmissive imaging spectrometer with a volume phase technology (VPT) holographic grating, an NIR optimized back-illuminated, deep-depletion charge-coupled device (CCD) detector, and a input port for fibre bundle 241. Raman signals collected by fibre bundle 241 may be provided to spectrometer 242. The holographic grating may disperse incoming light onto the CCD detector. The CCD detector may be liquid nitrogen-cooled and controlled by a computer. The Raman spectra associated with NIR autofluorescence background may be displayed on a computer screen in real time and/or saved for further analysis. Spectrometer 242 may acquire spectra over the wavenumber range of 800-1800 $cm^{-1}$ (equivalent to a wavelength range of 838-914 nm). The spectral resolution of a prototype system was 8 $cm^{-1}$. The diode laser may be selected from those lasers having a wavelength suitable for acquisition of spectra in the wavenumber range of 800-1800 $cm^{-1}$.

In some embodiments, a spectral adapter is placed between excitation light source 202 and scanner 204. In some embodiments, the spectral adapter does not displace or affect the laser beam in any manner due to dedicated optical design. The spectral adapter may ensure that the end face of fiber bundle 241 is always automatically in confocal alignment with the focal point of the excitation light inside a skin tissue. The spectral adapter may allow fiber bundle 241 to act as a confocal pinhole to facilitate confocal fluorescence imaging and confocal Raman imaging. This arrangement may also facilitate the alignment of a target microstructure for spectral analysis.

In some embodiments, imaging and spectral measurement may be performed using light from the same laser. For Raman spectral measurements, a frequency stabilized 785 nm diode laser may be used and reflectance confocal imaging may be performed under 785 nm. In an example embodiment, confocal Raman or Raman with autofluorescence background, or NIR autofluorescence imaging may also be performed by connecting fibre bundle 241 to a photodiode or other single channel detector. These two imaging modalities maybe performed simultaneously and may be co-registered. A transmittance reflectance narrow band filter may be used to facilitate Raman imaging of selected molecular vibration bands. Raman and/or NIR autofluorescence spectral measurements of an interested area (e.g. the whole or portion of a target microstructure) may be performed by directing the laser beam to scan only at the ROI.

In an alternative embodiment, a blue laser (or other short wavelength laser) may be used to obtain both reflectance confocal imaging and fluorescence confocal imaging simultaneously or in sequence and to perform fluorescence spectral measurements. In a further alternative embodiment, a femtosecond red wavelength or NIR wavelength laser may be used to simultaneously or nonsimultaneously perform two-photon fluorescence imaging, reflectance confocal imaging, and two-photon fluorescence spectral measurements. Confocal Raman imaging and Raman spectral measurements may also be performed using the same laser. Confocal reflectance imaging, two-photon fluorescence imaging, and confocal Raman imaging may be performed simultaneously and co-registered with the laser. Raman spectral measurements, NIR fluorescence spectral measurements, and two-photon fluorescence spectral measurements may be taken simultaneously with a spectrometer capable of covering a broad spectral wavelength range. In an alternative embodiment, second harmonic generation (SHG) imaging of skin collagens or other structural components may be performed with the same laser and same optical set-up by placing a narrow band pass filter before the lens to capture the second harmonic photons (half wavelength of the illumination laser).

The present invention has non-limiting example application to:
- non-invasive analysis of blood analytes, for the diagnosis of disease or physiological states by detection and measurement of the fluorescence and Raman spectra of subsurface blood vessels;
- non-invasive measurement of glucose levels in subsurface blood vessels;
- determining drug localization and drug concentration by detecting and measuring fluorescence and Raman spectra of such compounds in targeted microstructures such as blood and skin; and
- evaluating the status of skin for diagnosis and in response to therapeutic or cosmetic interventions.

Figure 6:
FIG. 6(a) to (c) are images of human skin taken using the multiphoton microscopy assembly of FIG. 5A.

FIG. 6(a) to (c) are (a) an RCM image (b) an integrated TPF and SHG image, and (c) an RCM/TPF/SHG overlay image extracted from in vivo videos of the skin of a Caucasian male volunteer obtained with a multiphoton microscopy assembly 200 as shown in FIG. 5A. Sampling procedures were the same as those for the images obtained in FIGS. 3 and 4 discussed above. An excitation wavelength of 720 nm was used. The field of view was 170 μm×170 μm, resolution at 256×256 pixels, and imaging frame rate was 15 fps. The images are of the stratum spinosum (SS). In the RCM image (FIG. 6(a)) the cellular membranes and intercellular materials are bright, while cytoplasm and nuclei in the center are dark. In the integrated SHG/TPF image (FIG. 6(b)) of the same layer, the cytoplasm is bright. The in vivo videos from which the images in FIG. 6(a) to (c) were extracted increased in depth from near the skin surface to the dermal/epidermal junction (DEJ). Honeycomb shaped cells in the SS showed bright cell boundaries in the RCM channel while bright cytoplasm was observed in the SHG/TPF channel. Deeper at the DEJ, dermal papilla and cellular structures were well visualized in both RCM and SHG/TPF channels. Some basal cells at the DEJ were bright in both the RCM and SHG/TPF channels, suggesting the cells contained melanin, which is both highly scattering and fluorescent.

Figure 5B:
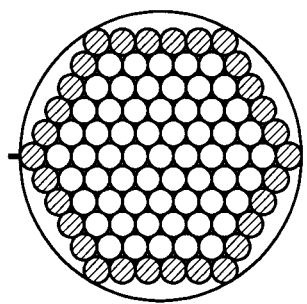
FIGS. 5B and 5C are cross sectional views taken along the planes B-B and C-C of fibre bundle of the multiphoton microscopy assembly shown in FIG. 5A.
Figure 5C:

Fibre bundle 241 is configured to increase the collection area of emitted photons for a high signal-to-noise ratio in spectral acquisition. An example arrangement of optical fibres 241 is shown in FIGS. 5B and 5C. Fibre bundle 241 has two different patterns at the input and output sides as shown in cross sections B-B and C-C from FIG. 5A in FIGS. 5B and 5C respectively. As denoted by the shaded circles, the outside fibers at the input side of fiber bundle 241 are mapped to the ends of the line pattern of fiber bundle 241 at the output side. In the example embodiment shown, fiber bundle 241 has 90 small fibres (single fiber diameter: 100 μm; numerical aperture (NA): 0.12) arranged in a hexagon pattern at the input end to provide a much larger collection area than a single fibre. The output end has all of the 90 fibres arranged as 2 straight rows with 45 fibres in each row so that most of the collected light can be coupled into the narrow entrance slit of spectrometer 242. The width of this elongated bundle of fibers is 200 μm. In some embodiments the f-number (f/#) of the spectrograph system (f/4) may be matched with the numerical aperture (NA) of the fiber (0.12) as: $f/\# = 1/(2 \times NA)$.

Since excitation light power and transmission efficiency of optical components can vary according to excitation wavelength, excitation power for excitation emission matrix (EEM) measurements in spectroscopy mode may be kept constant by adjustment by attenuator 203. In the alternative, attenuator 203 may be adjusted to compensate for (instead of eliminating) excitation power fluctuations.

TABLE 1

Performance of multiphoton microscopy assembly

| Parameter | Description |
|---|---|
| Imaging Lateral Resolution | ~0.5 μm |
| Imaging Axial Resolution (Estimated value based on lateral resolution) | ~1.5 μm |
| Field of View (adjustable) | 60 μm × 60 μm-500 μm × 500 μm |
| Imaging Speed | ~12 FPS |
| Laser Tuning Range | 720 nm-950 nm |
| Spectral Resolution | ~4 nm |
| Spectrometer CCD Data Resolution | ~0.48 nm/pixel |

Table 1 includes major performance parameters of an example embodiment of a multiphoton microscopy assembly according to the invention.

Some embodiments of the invention relate to computer control and electrical signal synchronization of assemblies such as 100 and 200, as described next.

Scanner/Detection Coordination

According to some embodiments, the scanner unit and detection unit are coordinated for improved performance.

The scanning unit includes scanners such as scanners 104 and 204 which scan the excitation light over a region of interest in the sample. The detection unit includes the detectors (e.g. PMTs) such as 118, 218 and 230, and frame grabber 122, 222 for image acquisition, and spectrometer 242 for excitation-emission matrix (EEM) measurement. In some embodiments, synchronization signals are generated as described next to coordinate image acquisition with scanner movement for accurate image display.

Figure 7:
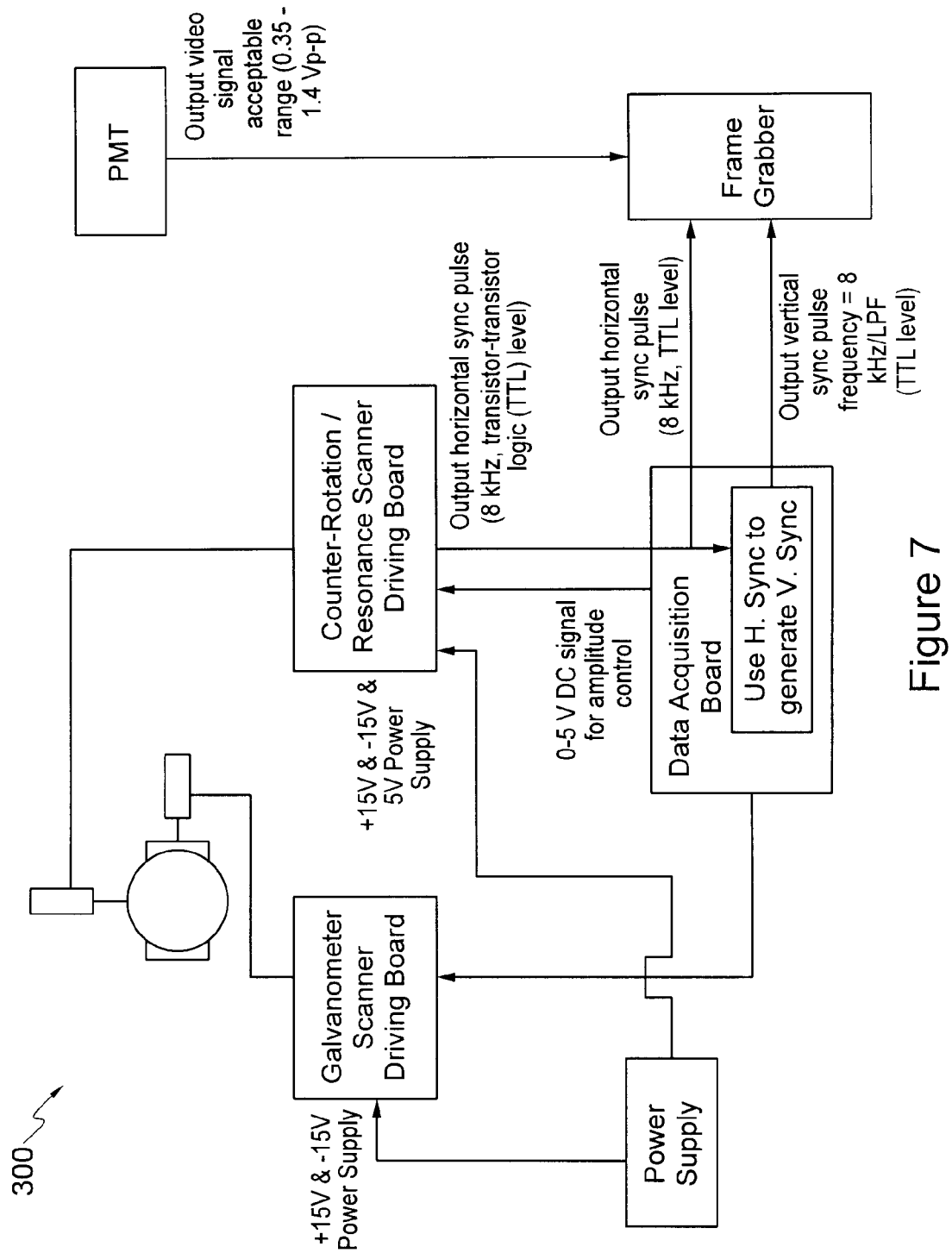
FIG. 7 is a schematic of a synchronization system for a multiphoton microscopy assembly according to an embodiment of the invention.

FIG. 7 shows an example synchronization system 300 for synchronizing image acquisition with scanner movement according to an example embodiment of the invention. A data acquisition (DAQ) board is used to generate the synchronization signals to coordinate the scanner and the detection units.

The DAQ board generates signals to drive the scanner axes. In some embodiments, one scanner axis (e.g. horizontal axis) may be scanned by a resonant scanner and the other scanner axis (e.g. vertical axis) may be scanned by a galvanometer scanner. For example, a DC signal may be used to set the scanning amplitude of the resonant scanner. For example, a voltage signal in a saw-tooth pattern may be used to drive each step of the galvanometer scanner. In some embodiments, the DAQ board may generate such exemplary control signals for each scanner as analog outputs. The resonant scanner outputs a horizontal synchronization pulse (H.Sync.), which has a rising edge at the beginning of each line scan. When the DAQ board receives this pulse, the DAQ board generates a voltage output to move the Y-axis scanner to the next line. Upon finishing scanning for one frame, the DAQ board will generate a vertical synchronization pulse (V.Sync.) to inform the Y-axis scanner to move to the beginning line for another frame. In this embodiment the frame size is set as 512×512 pixels. The DAQ board also transfers both of the synchronization signals to the frame grabber for display of video signals detected by PMTs.

Figure 8:
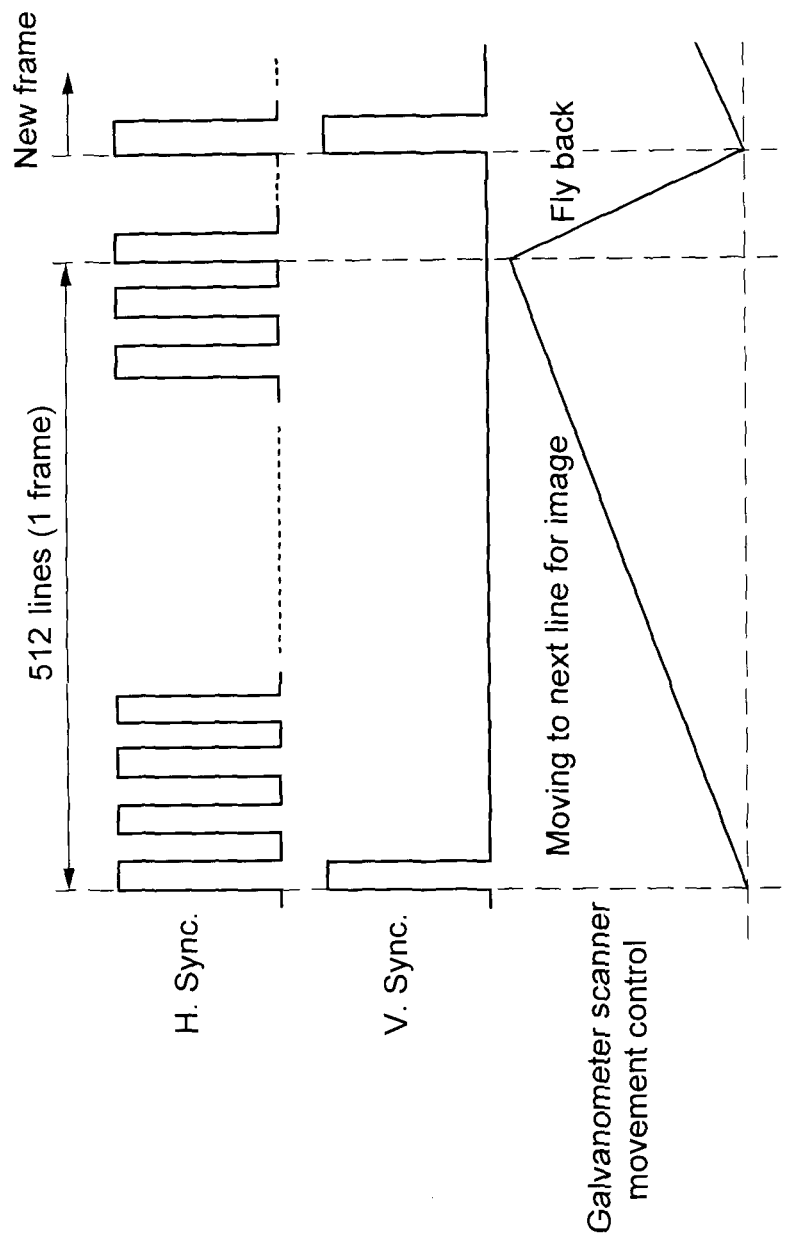
FIG. 8 is an illustration of signal synchronization of the synchronization system shown in FIG. 7.

As shown in FIG. 8, for each frame there are 512 H.Sync pulses representing 512 lines and one V.Sync pulse representing 1 frame. There is also a fly back duration for the galvanometer scanner (Y-axis) to safely move back to the starting line of a frame. All the signal edges, which overlap with the same vertical dotted line, are synchronized together.

Figure 9:
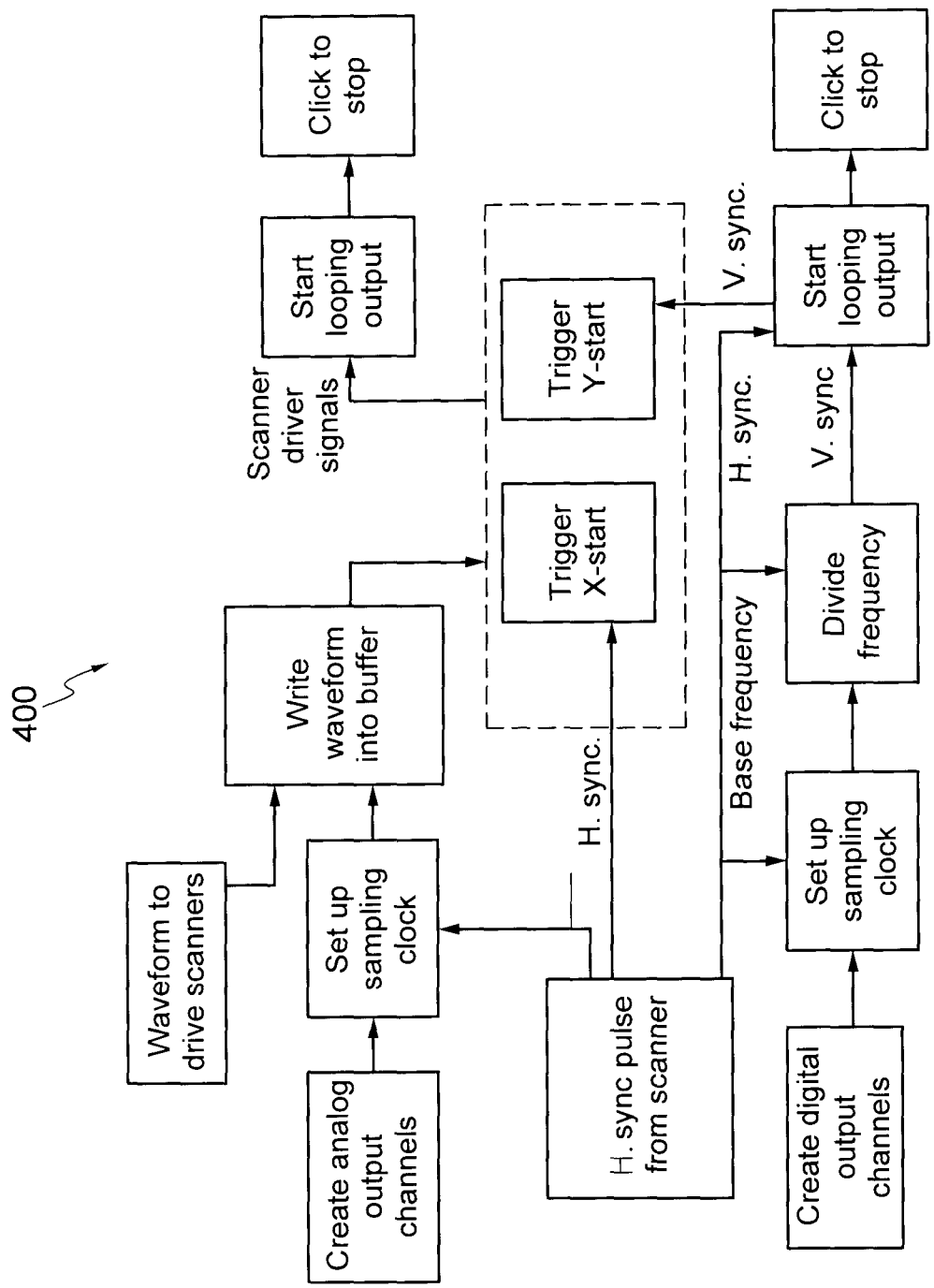
FIG. 9 is a flowchart illustrating a signal synchronization process for a multiphoton microscopy assembly according to an embodiment of the invention.

FIG. 9 shows a process 400 for controlling a DAQ board for signal reception and generation according to an example embodiment of the invention. Process 400 may be programmed into a suitable graphical development environment such as LabVIEW™. As shown in FIG. 9, the DAQ board receives H.Sync from the resonant scanner driving board and applies it as the sampling clock for generation of other digital and analog signals. The V.Sync is generated by frequency division using H. Sync as the base frequency. To generate the analog outputs, two waveform samples are written into buffers. Then the two buffers are triggered by H.Sync and V.Sync respectively to start outputting the analog waveforms to drive the two scanners (DC waveform for resonant scanner and saw-tooth waveform for galvanometer scanner).

Figure 10:
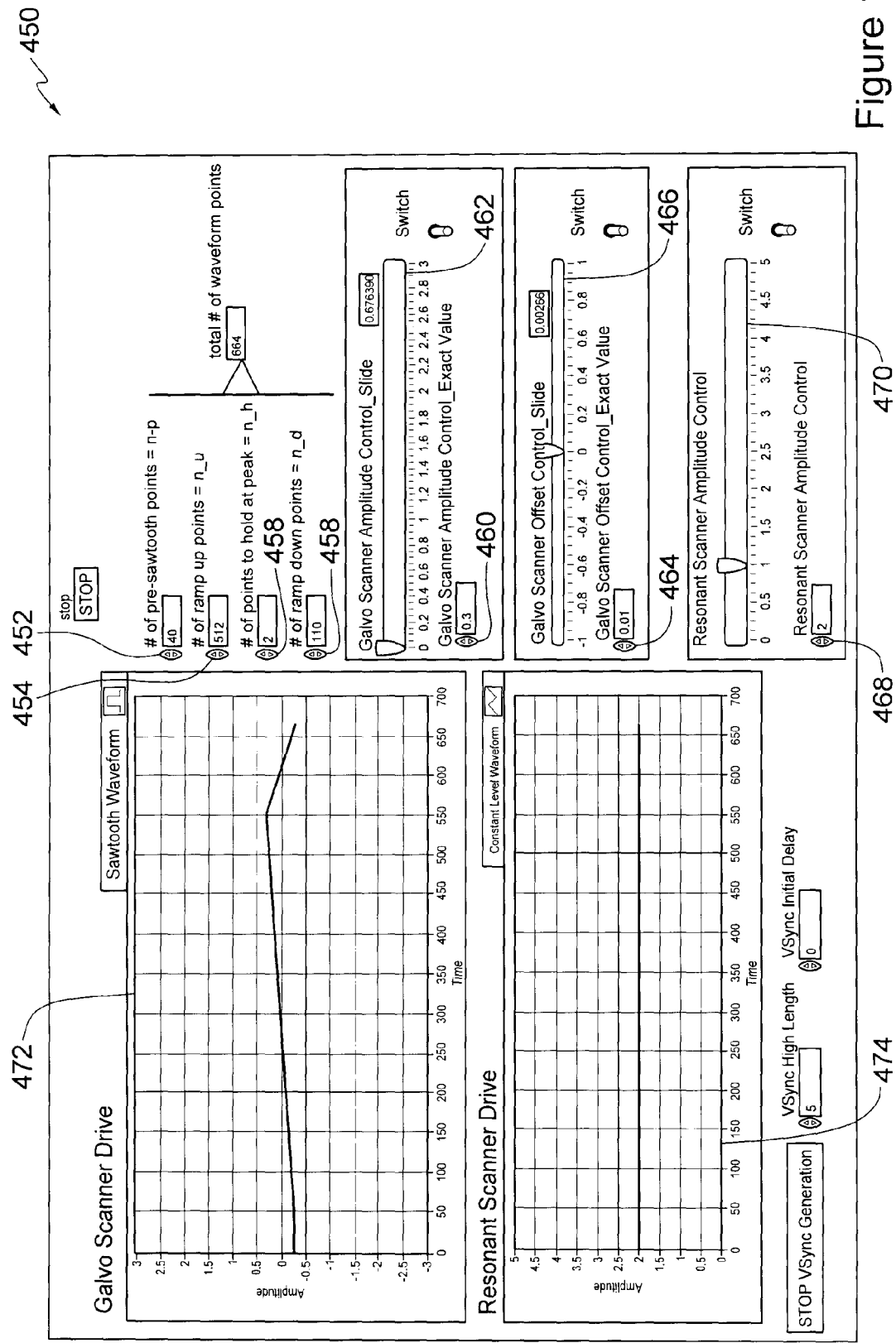
FIG. 10 is an illustration of a graphical user interface of a scanner control system for a multiphoton microscopy assembly according to an embodiment of the invention.

FIG. 10 is an example user interface 450 according to an example embodiment of the invention. The user may set the number of scanning lines for one frame. The number of waveform points may be set by control 452 for number of pre-sawtooth points, control 454 for number of ramp up points, control 456 for number of points to be held at peak, and control 458 for number of ramp down points. The amplitude of the galvanometer scanner can be adjusted in real time using either the exact number control 460 or smooth sliding bar control 462. The offset of the galvanometer scanner can be adjusted in real time using either the exact number control 464 or smooth sliding bar control 466. The amplitude of the resonant scanner can be adjusted in real time using either the exact number control 468 or smooth sliding bar control 470. The analog output waveforms are displayed in two oscilloscope style windows 472, 474.

Detector/Frame Grabber Coordination

According to some embodiments, the detectors and the frame grabber are coordinated for improved performance. The detectors may include detectors 118, 218 and 230, and frame grabber may include frame grabbers 122 and 222.

Where a PMT is used for photon detection, maximizing the gain of the PMT is desirable for high sensitivity photon detection. In some embodiments, PMT gain may be increased such that the resulting output voltage of the PMT (e.g. 3 V) is greater than the maximum input voltage (e.g. 1.4 V) of the frame grabber. In such embodiments, an attenuator may be used to attenuate the PMT output signal into an acceptable range for input to the frame grabber.

Figure 11:
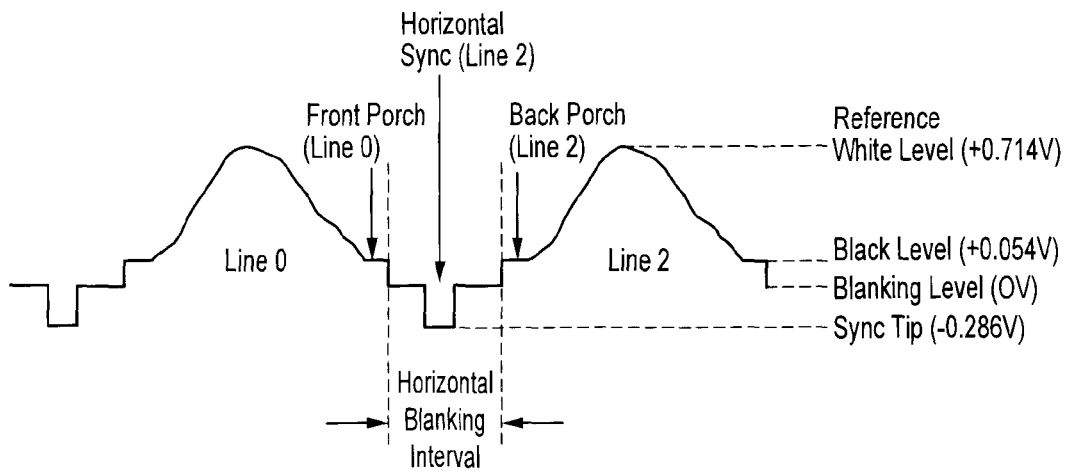
FIG. 11 is a graph illustrating setting the blanking level on a standard RS-170A video signal for a multiphoton microscopy assembly according to an embodiment of the invention.
Figure 12:
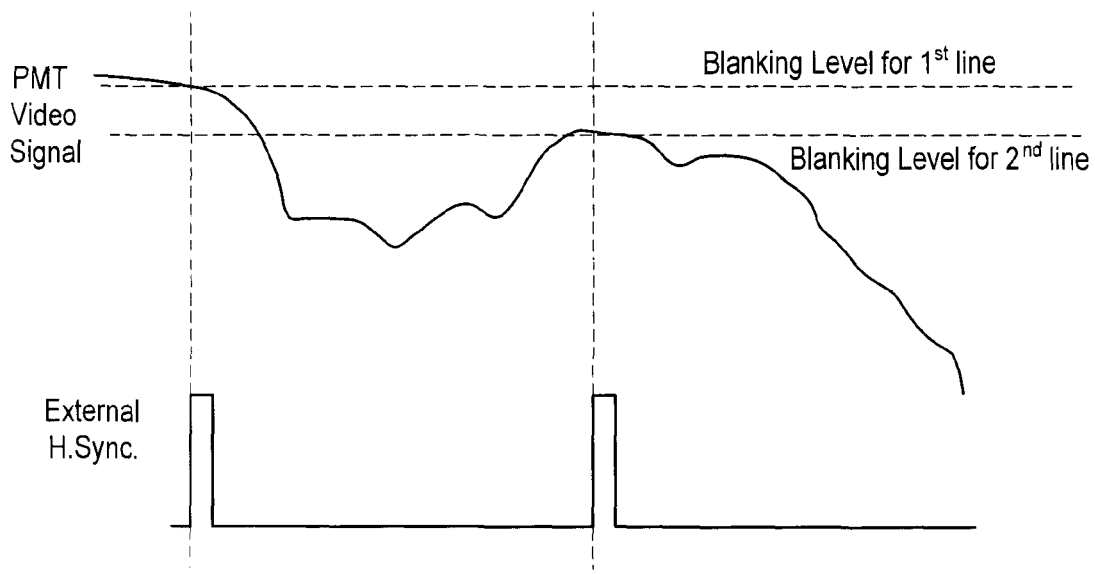
FIG. 12 is a graph illustrating setting the blanking level on a PMT video signal for a multiphoton microscopy assembly according to an embodiment of the invention.

Also in certain example embodiments, the frame grabber includes an 8-bit Analog to Digital Converter (ADC) module which will digitize incoming signal into 256 levels based on two reference levels: white (high) and black (low). A clamp circuit will assume the blanking level embedded in the video signal as zero, and set the high and low levels of ADC accordingly. In standard video signals, there is an H.Sync pulse and a blanking level embedded inherently for clamping. The clamp circuit will choose the voltage level right after the H.Sync as the blanking level: see FIG. 11. However PMT output is a continuous signal without any blanking level set. Thus the clamping circuit will clamp to an arbitrary voltage level on the PMT signal according to its relative position with the external H.Sync. In the case that the level chosen by the clamp circuit is relatively high, all the pixels in that line which are weaker than that level will be digitized as zero and displayed as black (see FIG. 12) resulting in loss of information due to this false setting of the reference level.

Figure 13:
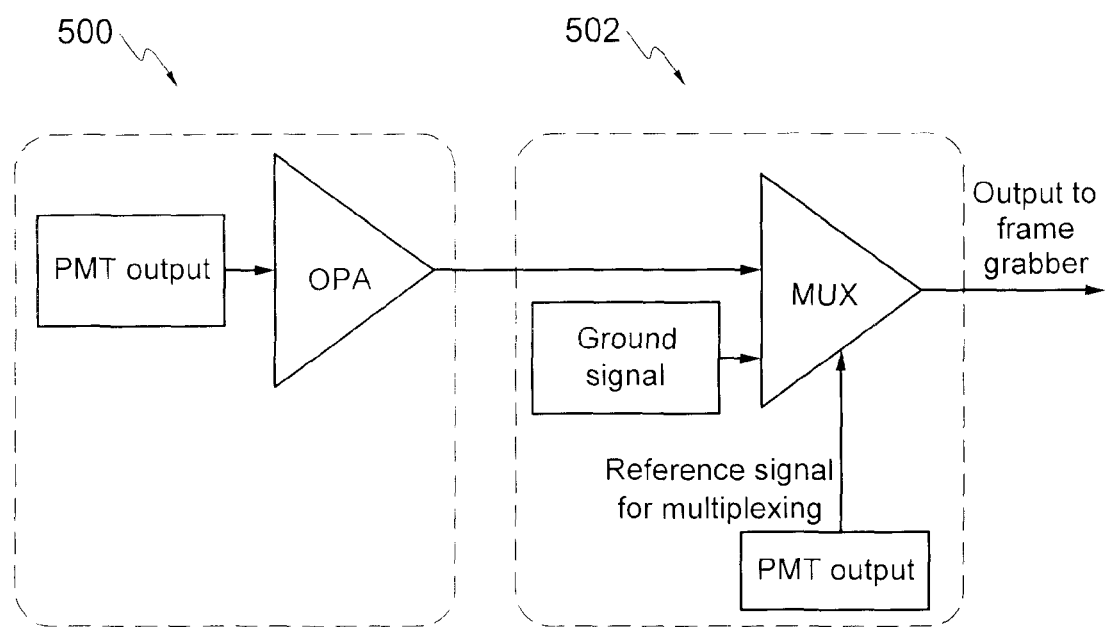
FIG. 13 is a schematic of an attenuator unit and multiplexer unit for a multiphoton microscopy assembly according to an embodiment of the invention.

FIG. 13 shows an attenuator unit 500 and multiplexer unit 502 according to an embodiment of the invention for addressing the above detector/frame grabber issues. Attenuator unit 500 attenuates the PMT output signal with an operational amplifier (OPA). Multiplexer unit 502 includes a multiplexer (MUX) which will choose either the PMT output or a ground signal as the input signal to the frame grabber. The external H.Sync (with a duty cycle<<50%) generated by DAQ board is input into the multiplexer as a digital reference signal. When the multiplexer detects a rising edge of H.Sync, it will choose to transmit the ground signal. Then the clamp circuit will assume this signal as the blanking level signal and set it as zero for the ADC. When the multiplexer detects a falling edge of H.Sync, it will transmit PMT video output to the frame grabber for image formation. In this way the clamp circuit can work properly with an appropriate setting of high and low reference levels of the frame grabber ADC.

Figure 14A:
FIGS. 14A and 14B are images of bovine collagen taken without and with an attenuator unit/multiplexer unit, respectively, of a multiphoton microscopy assembly according to an embodiment of the invention
Figure 14B:

FIG. 14A is an image acquired without attenuator unit 300 and multiplexer unit 302 and FIG. 14B is an image acquired with attenuator unit 300 and multiplexer unit 302. The images are of a bovine collagen sample and were acquired at 30 mW at 780 nm excitation, with a 100 µm×100 µm field of view. Each image includes signals collected with forward and backward scans of the resonant scanner. As can be seen from comparing FIGS. 14A and 14B, more signals were captured with use of attenuator unit 300 and multiplexer unit 302.

Image Distortion Correction

As mentioned above, resonant scanners such as resonant scanners 108, 208 are self-oscillating in a typical sinusoidal manner with varying speed, resulting in faster scanning in the middle of the scanning region and slower scanning at and near the edges. However, frame grabbers such as frame grabbers 122, 222 will presume that scanners are scanning at a constant speed, resulting in displayed images stretched at the edges of the images.

Assuming the focal length of the objective is D, the scanning angle of the resonant scanner is θ and the X-axis displacement of the excitation beam on the focal plane is S, the X-axis displacement is calculated as: $S=\tan(\theta) \times D$. The resonant scanner may have a scanning angle of ±15 degrees, for example. The relation $\tan(\theta) \approx \theta$ may be used to simplify the above equation as: $S \approx \theta \times D$. D is a constant and S will be linearly proportional to the scanning angle θ. Thus to simplify the theoretical calculation and processing procedure, the scanning angle θ of the resonant scanner may be used to represent the X-axis displacement of the excitation beam on the focal plane.

Figure 15:
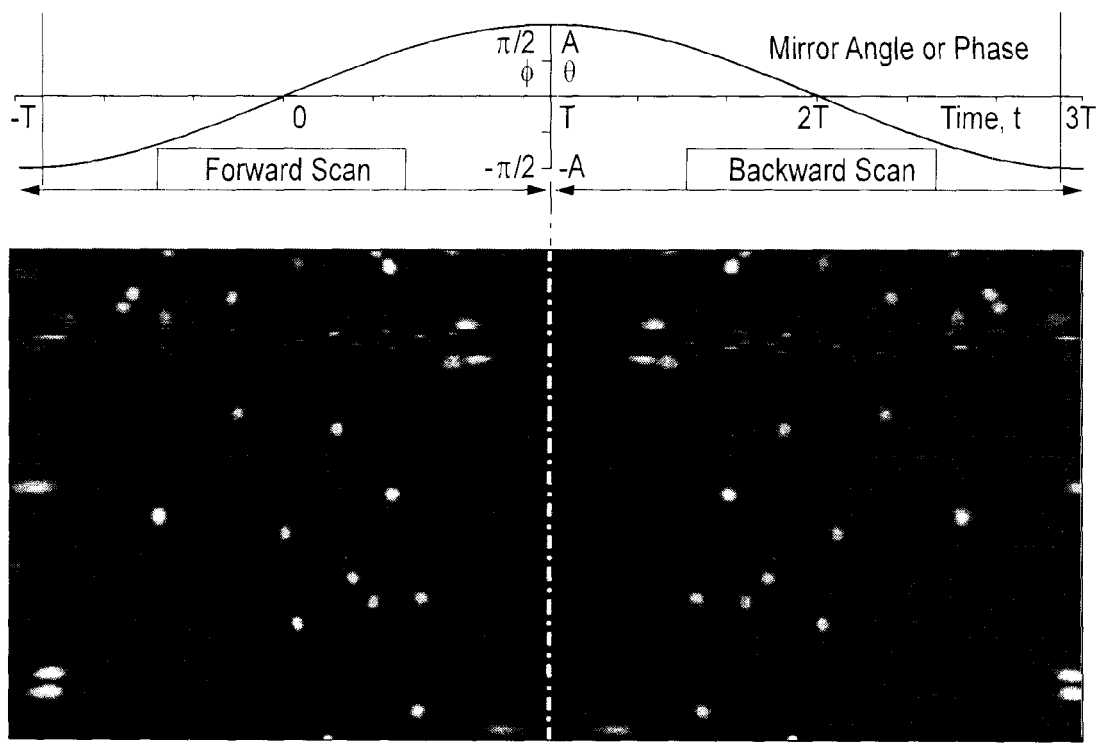
FIG. 15 is a plot of the scanning angle of a resonant scanner and a sample image taken with a multiphoton microscopy assembly according to an embodiment of the invention.

FIG. 15 shows the scanning angle of a resonant scanner such as resonant scanner 106 and 206. One period includes forward and backward scans over the same scanning range. Thus the backward scan generates a mirror image of the forward scan. As seen in the image of fluorescence beads, the beads at two edges of the scanning area are stretched along the X-axis. The images are TPF images of fluorescent beads at 30 mW at 780 nm excitation, 100 μm×100 μm field of view.

Figure 16:
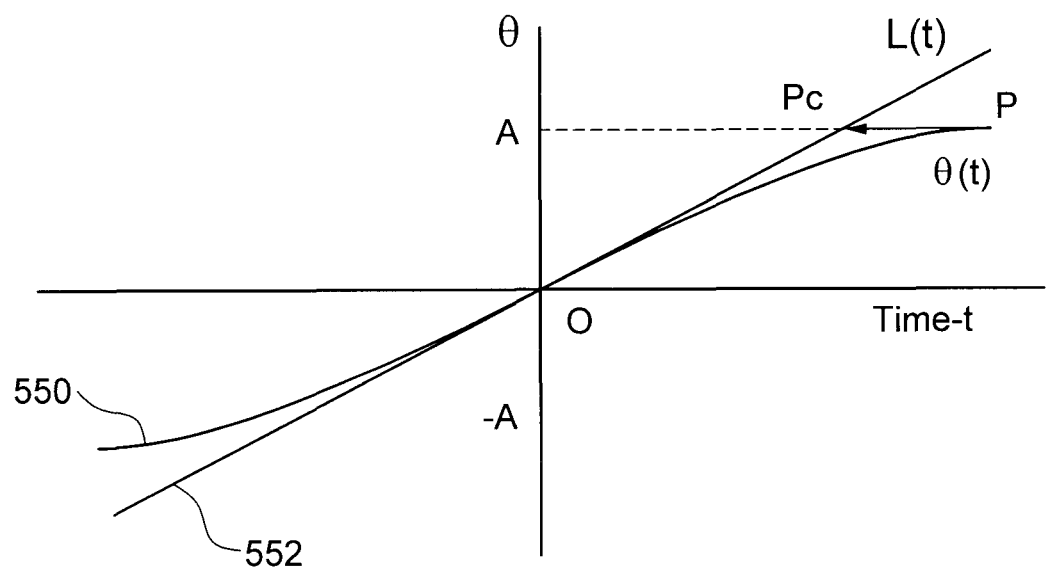
FIG. 16 is a plot illustrating a linearization algorithm for a multiphoton microscopy assembly according to an embodiment of the invention.

FIG. 16 graphically illustrates a linearization algorithm according to an embodiment of the invention to correct this distortion. The algorithm relocates each pixel to the position as a linear scan so that it is not distorted from the true shape. The following description of the algorithm focuses on processing the forward scan part. The scanning phase step size for each pixel is calculated as $\Delta\phi=2\pi/n$, where n is the pixel number per line (e.g. n=1024 for the image with 512×512 pixels because the forward scan and backward scan of X-axis scanner are symmetric) and 2π represents the resonant scanner sweeps for one period per line. The phase for each pixel location is $\phi=\Delta\phi \times$Pixel Number. The parameter Pixel Number is the pixel differences between the current location and the center pixel of the forward scan which is n/4. The correction factor for relocation is calculated as $C=\phi/\sin\phi$.

As shown in FIG. 16, curve 550 is the actual sinusoidal scanning pattern and line 552 is the ideal linear scanning pattern. θ(t) is a variable representing the actual scanning angle of X-axis scanner at a certain time point (t); A represents a certain value of θ(t); L(t) represents the corrected angle of X-axis scanner for the ideal linear scan. The pixel positioned at P on actual curve 550 is reassigned to position PC on ideal line 552 to correct the distortion using the correction factor $C=\phi/\sin\phi$ using an image processor. Image processing may be done in real-time.

Figure 17A:
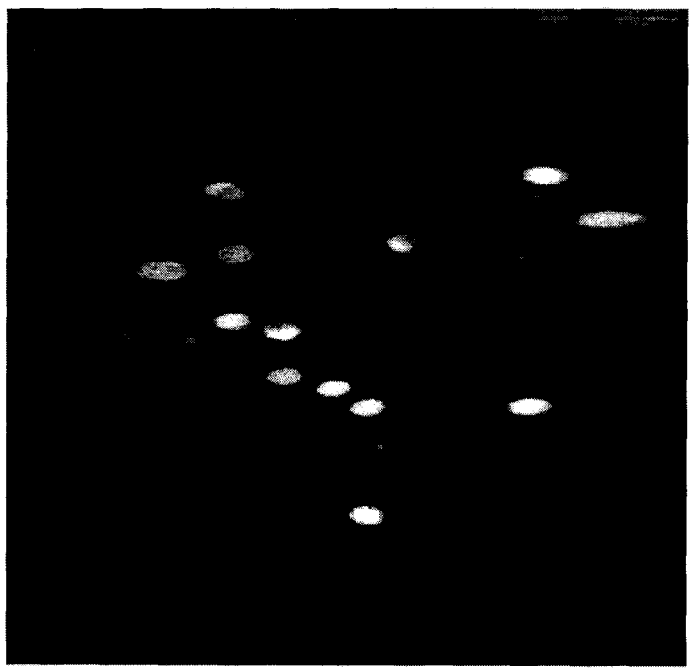
FIGS. 17A and 17B are sample images taken without and with, respectively, correction with a linearization algorithm for a multiphoton microscopy assembly according to an embodiment of the invention.
Figure 17B:
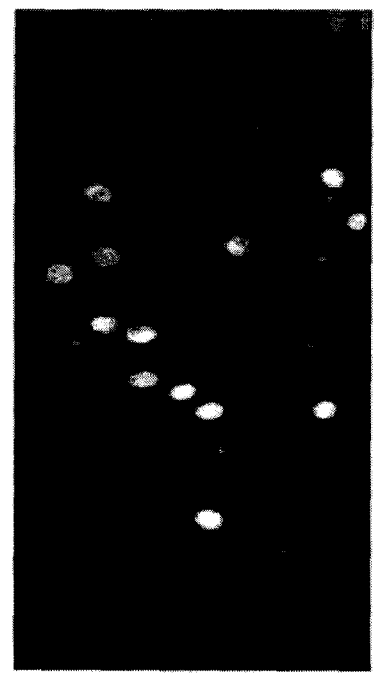

In FIGS. 17A and 17B, images of fluorescence beads are compared before and after applying the correction factor. There is almost no change for the beads in the center of the images before and after processing. While the beads at the two edges in FIG. 17A are obviously stretched along X-axis they are returned to their round shape after correction as shown in FIG. 17B.

Spectral Data Acquisition

In some embodiments, spectral data collected by spectrometers such as spectrometer 242 are processed and summarized as an excitation emission matrix (EEM). EEM is a matrix of emission intensity as a function of the excitation and emission wavelengths.

In some embodiments, the laser excitation wavelength is tuned, for example, in 10 nm steps. In some embodiments, tuning may be done over a range somewhat narrower than the specified range of the laser as the laser may not be able to be constantly mode-locked at some extreme wavelengths of the tuning range. Hence for a laser with a specified range of 720 nm to 950 nm, a tuning range of 730 nm-920 nm may be selected so that accurate EEM acquisition can be achieved for all excitation wavelengths. An emission spectrum for each excitation wavelength is collected with the spectrometer. The spectral data is processed and summarized into a matrix. The spectral data may be plotted for example as a contour map for analysis.

Figure 18:
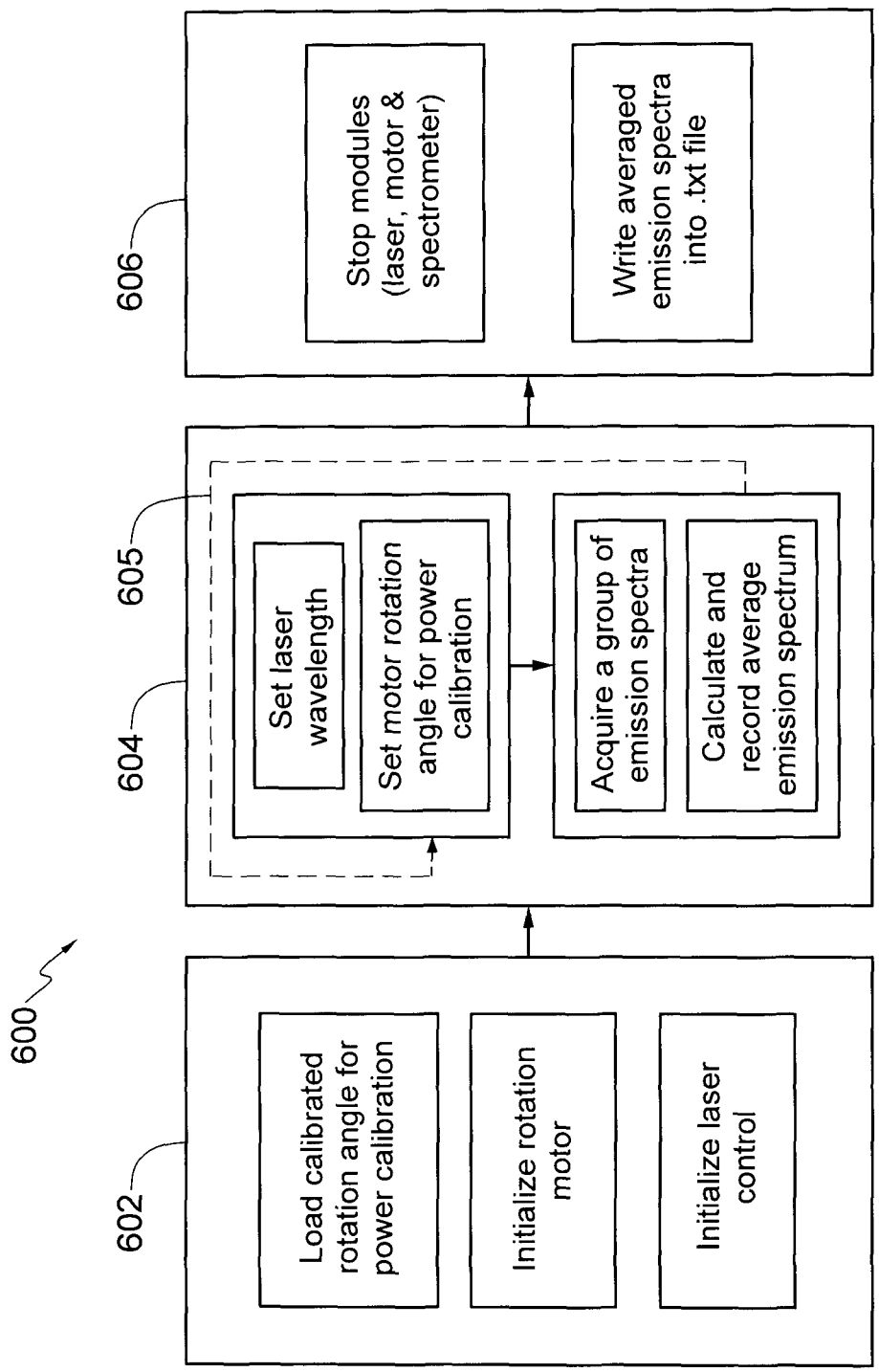
FIG. 18 is a block diagram illustrating a process for excitation power calibration of a multiphoton microscopy assembly according to an embodiment of the invention.

FIG. 18 illustrates an EEM acquisition process 600 according to an example embodiment of the invention. Process 600 may be programmed in a suitable graphical development environment such as LabVIEW™. Process 600 may use a time sequence structure to coordinate the components of a multiphoton microscopy assembly such as assembly 100 and 200 relating to EEM acquisition including the laser, the attenuator, and the spectrometer, namely the EEM sub-system. Automatic EEM acquisition minimizes the time spent on adjustment of device settings for the next excitation step, which helps to decrease the chance of photobleaching and photodamage of the tissue being investigated. In some embodiments, calibrations of the EEM sub-system are repeated as long as there is any change in optics setup or optical component alignment.

In FIG. 18 the blocks with thick outlines and thick arrows set the timing order of process 600. In the first block 602, a data file of rotation angles for the optical power attenuator motor is loaded, which is acquired with the excitation power calibration (described further below) and maintains the excitation power at a constant level for different excitation wavelengths. Simultaneously, a control module (e.g. ActiveX™ control) is loaded for attenuator motor rotation control and initializing an electrical communication path for laser control. After all of the tasks in block 602 are completed process 600 proceeds to block 604.

The second block 604 involves a loop 605 comprising acquiring multiple emission spectra for each excitation wavelength, calculating and recording the average spectrum, returning to the start of the frame to set a new excitation wavelength and new rotation angle of the optical power attenuator, and then acquiring another group of emission spectra. Loop 605 may continue until all emission spectra have been acquired.

Figure 19:
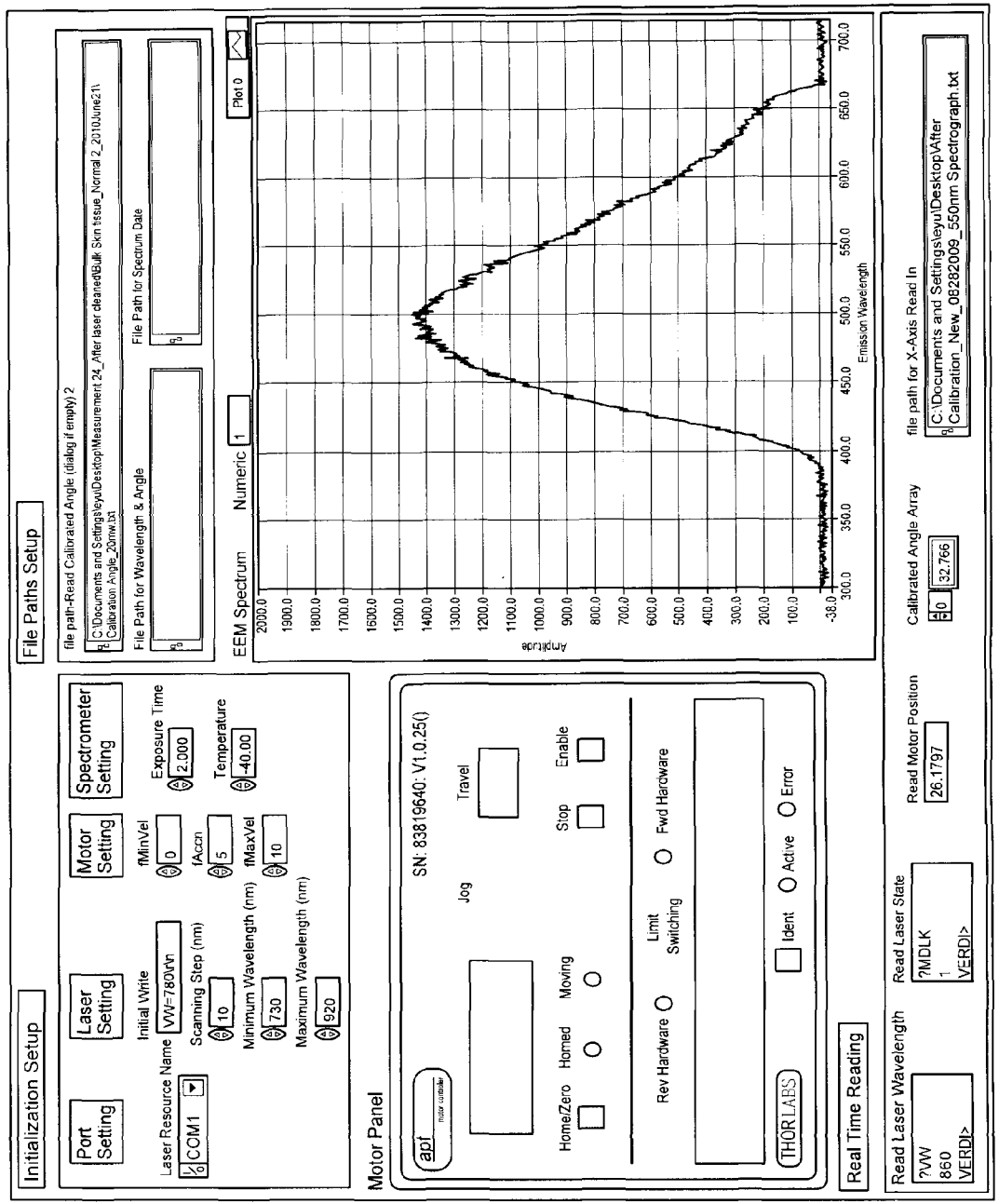
FIG. 19 is an illustration of a graphical user interface for a system embodying the process shown in FIG. 18.

Process 600 will then advance to block 606 to stop the system modules including the laser, attenuator motor and spectrometer, and save averaged spectra data (e.g. a .txt file). A separate program for single spectrum acquisition can be applied to measure the background spectrum either before or after EEM acquisition, which may require the operator to manually close the laser shutter. FIG. 19 shows a LabVIEW™ graphical user interface 650 of process 600. Basic settings can be changed directly on the interface such as laser scanning range and step width, attenuator motor rotating speed, and spectrometer exposure time. The interface may display real-time settings of key parameters including the excitation wavelength of the laser, angle of the optical power attenuator motor, and emission spectra under specific excitation wavelengths. The interface may also provide the operator with the number of groups of data that have already been acquired and a record of progress. Finally a standard "Save As" window may pop up to let the operator choose where and how to save the spectral data.

Excitation Power Calibration

Figure 20:
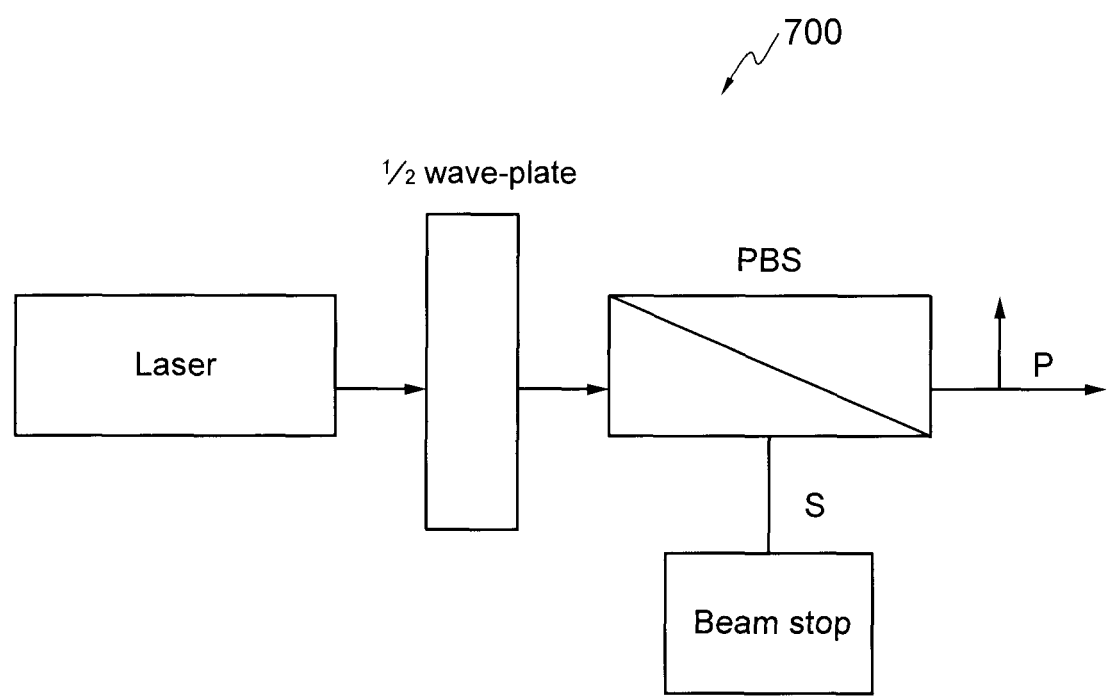
FIG. 20 is a schematic showing a power attenuator system for a multiphoton microscopy assembly according to an embodiment of the invention.

To compare the emission spectra under different excitation wavelengths, it is desirable to calibrate the excitation power to maintain it at a constant level over the entire excitation wavelength tuning range. FIG. 20 shows a power attenuator system 700 similar to power attenuator 203 for assembly 200. The intensity I of the polarized light that passes through the polarization beam splitter (PBS) is given by:

$$I = I_0 \cos^2(\theta) \quad (1)$$

Where $I_0$ is the input intensity and $\theta$ is the angle between the beam's polarization direction and the optical axis of the PBS. The half wave plate is mounted on a motorized rotational stage. As the half wave plate is rotated, the direction of the laser beam polarization varies continuously. Then the angle between the beam polarization and the PBS optical axis will change continuously and cause the excitation power to be attenuated by a varying ratio according to Equation (1). Therefore, excitation power can be controlled by adjusting the rotation angle of the half wave-plate. When the half wave-plate is rotated by an angle $\theta$, the laser beam polarization will be rotated by an angle $2\theta$. Thus the relation between output power of the attenuator and rotation angle of the half wave-plate is: $I = I_0 \cos^2(2\theta + \theta_0)$ according to Equation (1), where $\theta_0$ is the initial angle between laser beam polarization and the PBS optical axis, and $\theta$ is the rotation angle of the half wave-plate.

Figure 21:
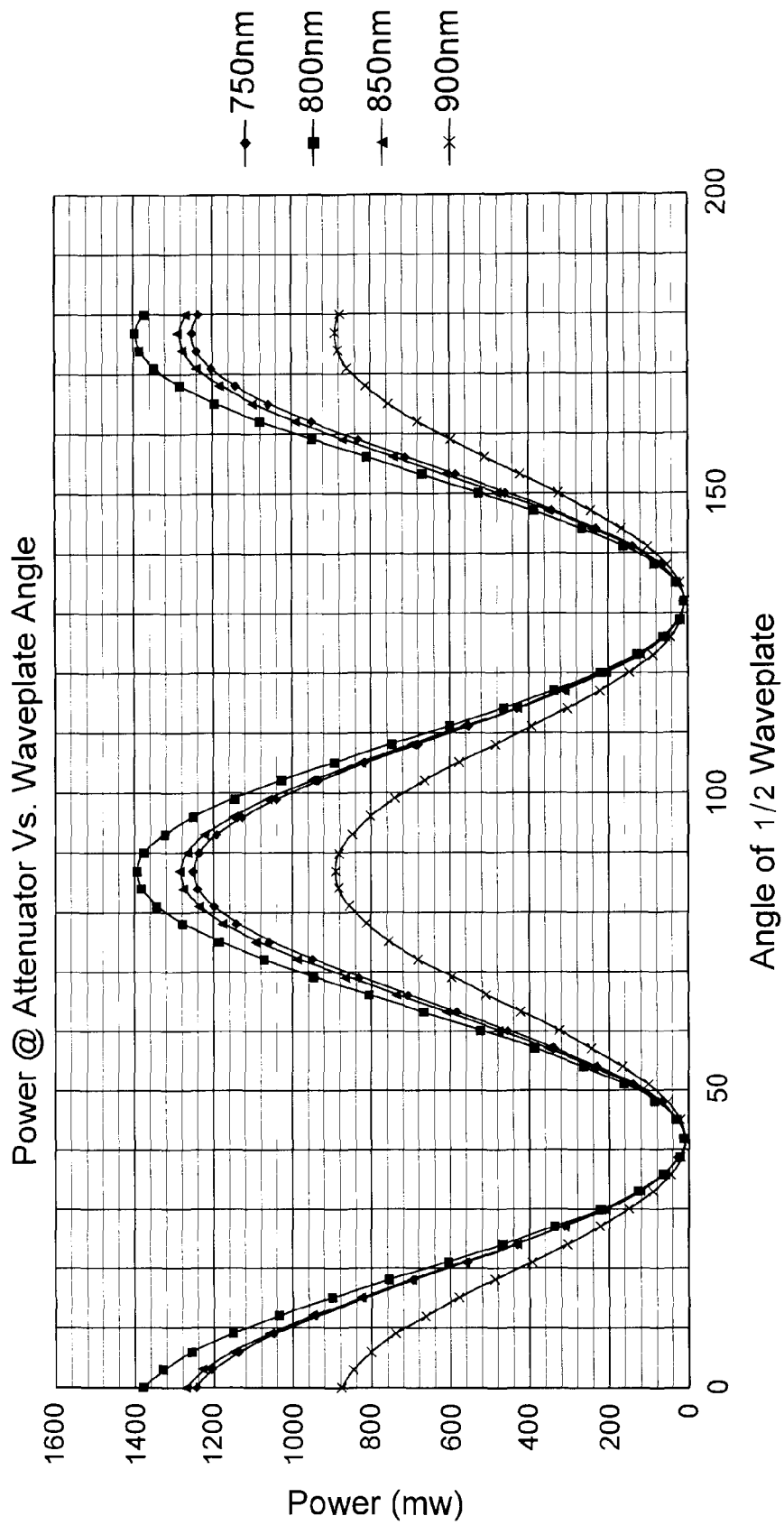
FIG. 21 is a graph plotting excitation power against attenuator motor rotation angle for a multiphoton microscopy assembly according to an embodiment of the invention.

Excitation power calibration may be performed in two steps. In the first step, the half wave plate (e.g. half wave plate 203') is rotated from 0-180° and excitation power is measured after the power attenuator for different angles of rotation. The curve shown in FIG. 21 shows generally how the excitation power changes (increase or decrease) with the increase of motor rotation angle so that the automated calibration program can be programmed to adjust the angle of rotation motor to attain the target value of excitation power. Four of these curves are shown in FIG. 21 for various excitation wavelengths (750 nm, 800 nm, 850 nm, 900 nm).

In the second step, the rotation angle of attenuator (e.g. attenuator 203) for each excitation wavelength is calibrated to maintain the excitation power after the objective (e.g. objective 210) at a constant level for all excitation wavelengths. Desired excitation power and an initial excitation wavelength may be inputted into an automatic program which outputs the power after the objective and adjusts rotation angle of the half wave plate (e.g. half wave plate 203') accordingly. The automatic program will keep reading current power and adjusting attenuator rotation angle until the desired excitation power is reached. Then the automatic program will progress to the next excitation wavelength and repeat steps as above. Finally the automatic program will record a group of calibrated rotation angles for each excitation wavelength (730 nm-920 nm, 10 nm step size). This set of angles will be input to an EEM acquisition program, such as process 600, for automatic adjustment by the power attenuator to provide a constant level of excitation power for all excitation wavelengths.

Figure 22:
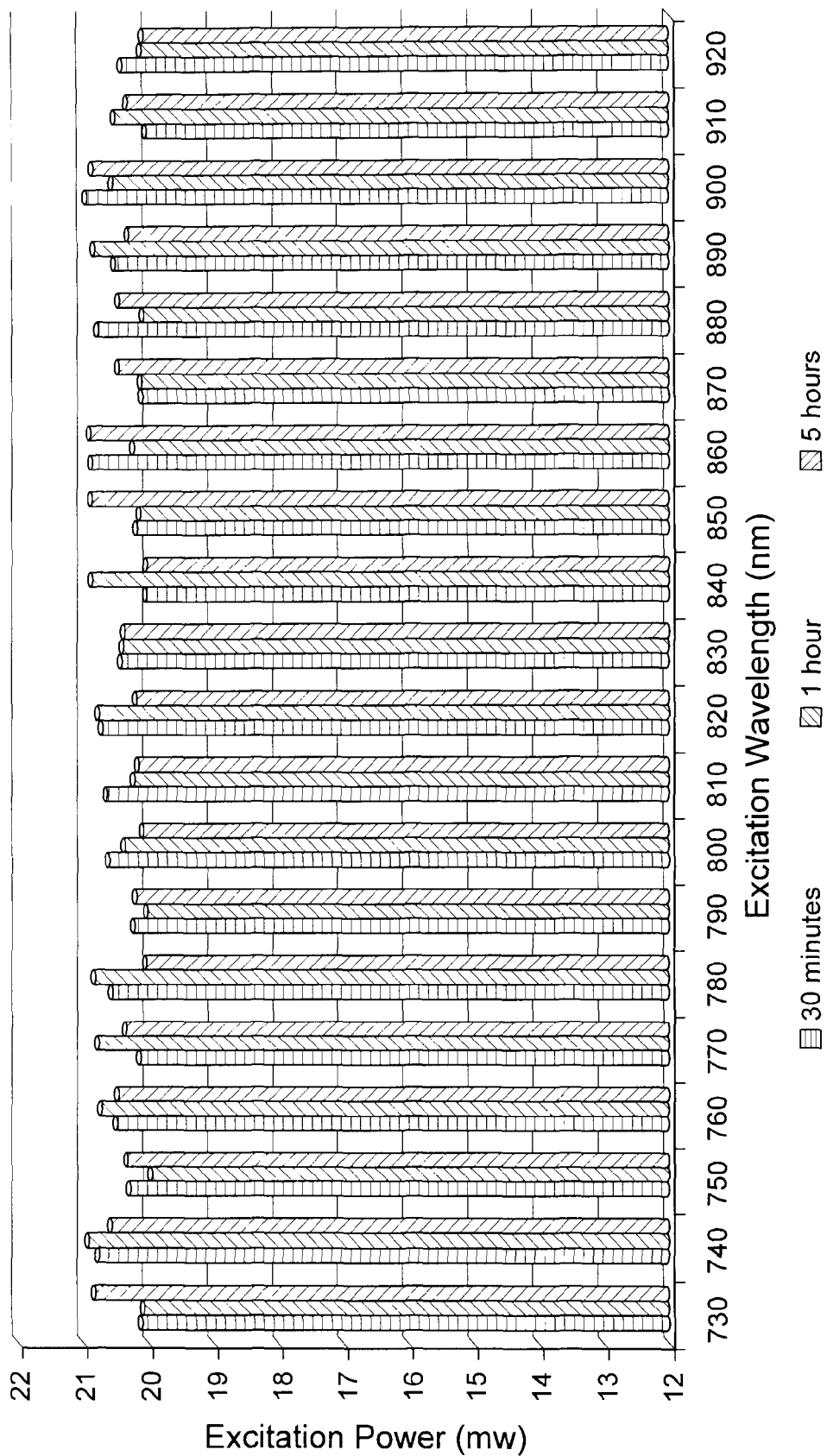
FIG. 22 is a graph illustrating fluctuation of excitation power across different wavelengths over time.

FIG. 22 shows how excitation power fluctuates due to inherent instability and operation noise of a mode-locked laser. Excitation power for different wavelengths was measured with the rotation angles of attenuator set as that recorded in the previous calibration. Three groups of data were collected at different times after the laser has been turned on (30 minutes, 1 hour and 5 hours), as shown in FIG. 22. The fluctuations are all within ±5% of the desired power (20 mW), which will not have significant influence on EEM acquisition. Therefore according to some embodiments of the invention, it will suffice to implement power calibration at the commencement of EEM acquisition. In other embodiments where the laser is very stable, calibration may not be necessary.

Laser Spectral Bandwidth Measurement

When the spectral bandwidth of a laser excitation beam becomes wider than the fluorophore absorption window, two-photon absorption efficiency is reduced. This affects TPF emission intensity. Spectral bandwidth of an excitation beam over the laser tuning range from 730 nm to 950 nm was measured for a multiphoton microscopy assembly according to an example embodiment of the invention. After transmitting through the excitation path and objective lens, the laser light was collected by an integration sphere. The collected light was sent to a spectrometer through a fiber bundle for spectral measurement. The spectral bandwidth is calculated as the FWHM of the spectrum. Three groups of measurements were taken with forward and backward tuning of the laser in each group, as shown in FIG. 28. All of six sets of data show good agreement with each other, with spectral bandwidth ranging from ~6 nm to ~14 nm.

Imaging Resolution Measurement

According to Equation (2), the number of two-photon fluorescence photons collected per unit time should be proportional to the fluorescence collection efficiency $\phi$ of the measurement system, which is dependent on the numerical aperture (NA) of the objective (e.g. NA=1, magnification=60 for Olympus model no. LUMPLFLN60XW). Resolution is inversely proportional to NA of the objective. Thus the detected intensity of two-photon emission will be affected by resolution.

It is desirable to measure resolution for different excitation wavelengths. Optical resolution can be defined as the shortest distance between two points on a sample which can be differentiated from each other as individual entities. When emitted light from different points on a sample is collected by the objective and reconstructed as an image, light from each point will generate a pattern described as a point spread function (PSF). The FWHM of a central bright region of the PSF is usually specified as the optical resolution. The FWHM of the PSF in the x-y plane (lateral resolution) for a two-photon microscope can be calculated as:

$$FWHM_{xy} = \frac{\sqrt{2\ln 2} \times 0.325\lambda}{NA^{0.9}} \quad (3)$$

For comparison, the FWHM of the PSF for a single-photon fluorescence microscope is expressed as:

$$FWHM_{xy} = \frac{0.61\lambda}{NA} \quad (4)$$

Figure 23A:
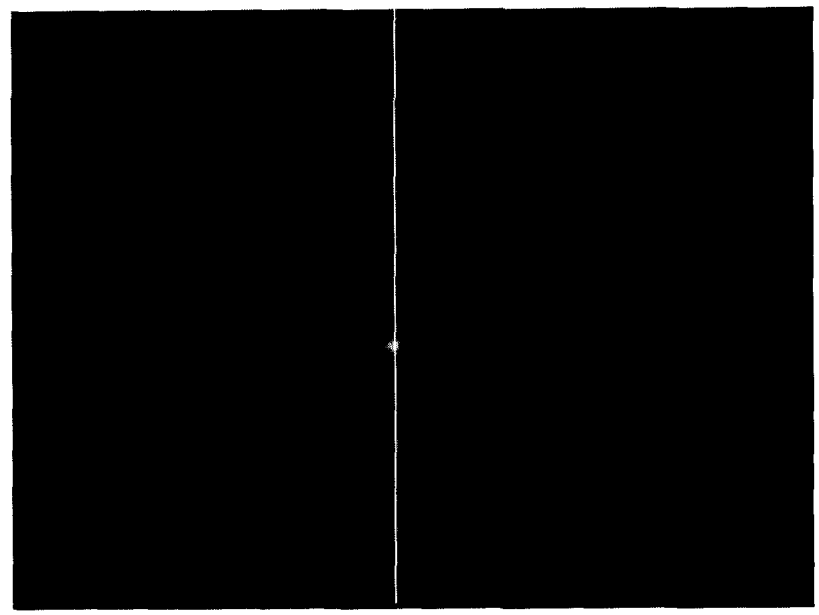
FIGS. 23A and 23B are, respectively, a TPF image of a fluorescent bead taken with a multiphoton microscopy assembly according to an embodiment of the invention, and a plot of the intensity of the distribution of the pixels along the vertical line on the image.
Figure 23B:
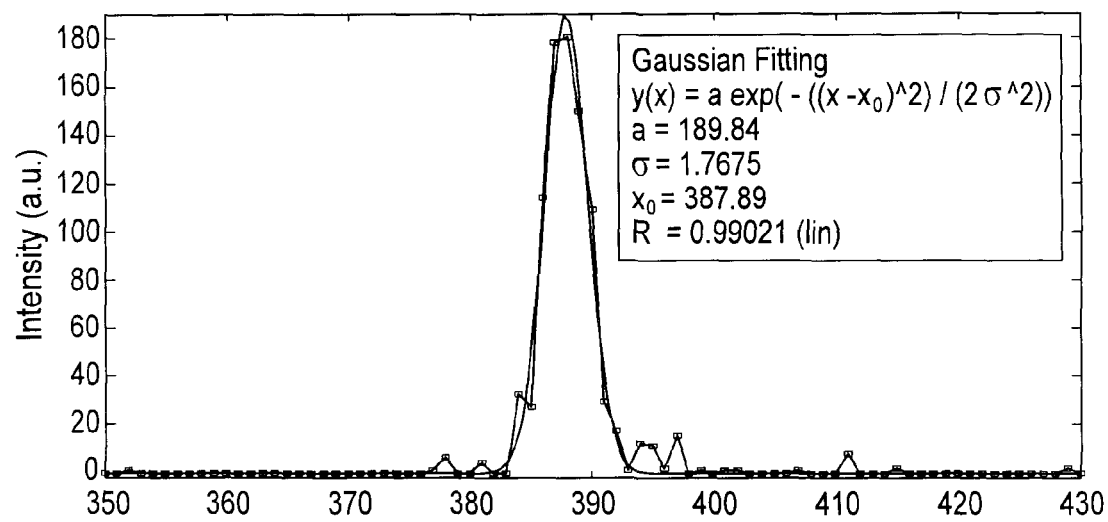

To measure the PSF, fluorescent micro beads with a diameter smaller than the FWHM of the PSF are used. The fluorescent bead used in this measurement has a diameter of $\Phi=116$ nm, which is much smaller than the theoretical resolution of two-photon microscope (~400 nm). The beads were suspended in water and sonicated by an ultrasonic water-bath to further separate the beads. The bead suspension was then blended with silicon gel. The mixture was dried. The dried mixture was placed on a plastic plate for measurement. Using a particular excitation wavelength, TPF image of the beads was acquired and a line drawn across the centre of the bead on the image as shown in FIG. 23A. The image was taken at an excitation wavelength of 820 nm and a field of view of 60 μm×60 μm, where each pixel is approximately related to an actual size of 0.1 μm×0.1 μm on the sample. Intensity distribution along this line was plotted and fitted to a Gaussian curve using a MATLAB™ program as shown in FIG. 23B. FWHM of the curve is calculated as the resolution value. Several beads are measured and an average value of resolution was obtained for that specific excitation wavelength.

Figure 24:
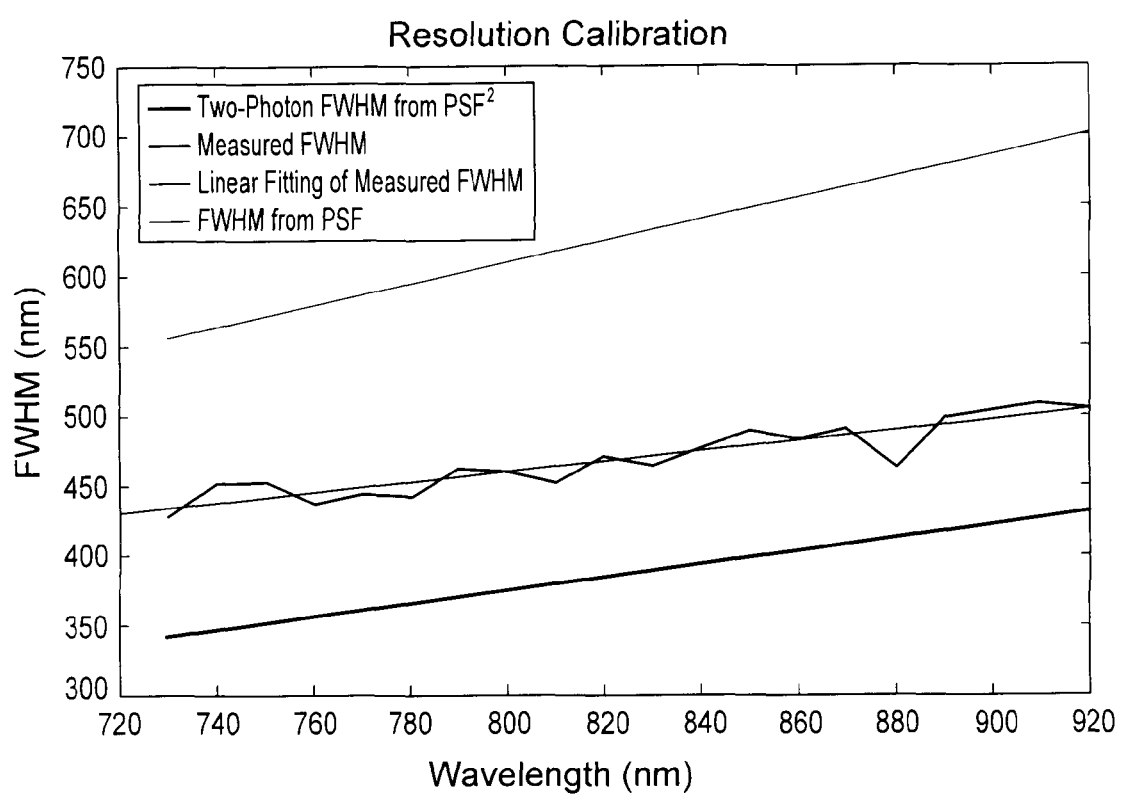
FIG. 24 is graph plotting TPF resolution against excitation wavelength for a multiphoton microscopy assembly according to an embodiment of the invention.

The relation between the measured resolutions and excitation wavelengths is plotted in FIG. 24. For comparison, theoretical resolutions of two-photon and single-photon fluorescence are also shown in FIG. 24, which are calculated based on Equation (3) and (4) respectively. A linear fitting of the experimental data is also provided. The average degree of experimental resolution is higher than the theoretical value due to variations of refractive index and scattering effects in tissue samples. However, the experimental resolution is still approximately proportional to the excitation wavelength, which is similar to the theoretical calculation. These results indicate that the resolution values are in a reasonable range, and therefore will not have significant influence on EEM analysis.

Wavelength calibration of the spectrometer may be done with a Hg (Ar) lamp, for example. Calibration of the emission beam path intensity may be done with an NIST calibrated tungsten lamp, for example.

The above-discussed calibrations and measurements allow for more accurate and reliable EEM measurements to be made with multiphoton microscopy assemblies according to some embodiments of the invention.

Experiments on Biological Samples

Multimodal imaging, such as TPF, SHG and confocal imaging, have different contrast mechanisms. Multimodal imaging can be applied to reveal various morphological characteristics of skin, for example. In some embodiments, integration of multiple imaging modes provides a useful preview of a region of interest to guide the acquisition of EEM and more comprehensive information for analysis.

Figure 25A:
FIG. 25(A) to (C) are images of human skin obtained with a multiphoton microscopy assembly according to an embodiment of the invention.
Figure 25B:
Figure 25C:
Figure 26:
FIG. 26 is an image of human skin obtained with a multiphoton microscopy assembly according to an embodiment of the invention.

FIGS. 25 and 26 are images of excised normal skin from the human scalp obtained using a multiphoton microscopy assembly according to an example embodiment of the invention. The excised skin samples were obtained from the surgery unit of the VGH Skin Care Center, Vancouver, Canada. Using a microtome, 20 μm-thick cross sections were sliced from frozen skin tissues. The sections were placed between a microscope slide and cover glass and stored at 4° C. until analyzed. The samples were irradiated with 785 nm femtosecond laser pulses under 30 mW excitation power with a field of view of 150 μm×150 μm. The combined images combine the confocal, SHG and TPF channels.

As shown in FIGS. 25A to 25C, clear fibrous structures are observed in all three channels, indicating the sample is in the dermis compartment which mainly comprises extracellular fiber structures. FIG. 25A shows the confocal signal. The SHG signal (FIG. 25B) mainly comes from collagen fiber and the TPF signal (FIG. 25C) may come from elastin and/or collagen fibers. As seen in the combined image (FIG. 26), there is no overlap between the TPF and SHG signals, indicating the TPF signal mainly originates from elastin fibers.

The combined image in FIG. 26 shows various morphological structures of tissue compositions and relative distribution and density of these compositions. The results also assist in distinguishing TPF of elastin fiber from that of collagen fiber, which is comparatively difficult using spectral analysis. In some embodiments, imaging provides a preview of the tissue sample in advance so that EEM can be acquired from interesting regions of skin tissues. More comprehensive information may be obtained by using the imaging channels together with nonlinear EEM analysis.

Imaging-Guided Nonlinear Excitation-Emission-Matrix (EEM)

To assist nonlinear EEM analysis of skin tissues, EEM measurements of pure endogenous fluorophores of skin tissue including elastin, collagen, keratin, NADH, FAD and melanin were obtained. Single-photon EEMs were measured by tuning the excitation wavelength from 250 nm to 600 nm using a known commercial system (FluoroLog3™). A multiphoton microscopy assembly according to an example embodiment of the invention was used. The assembly was tuned from 730 nm to 920 nm and was used for two-photon EEM.

Figure 29A:
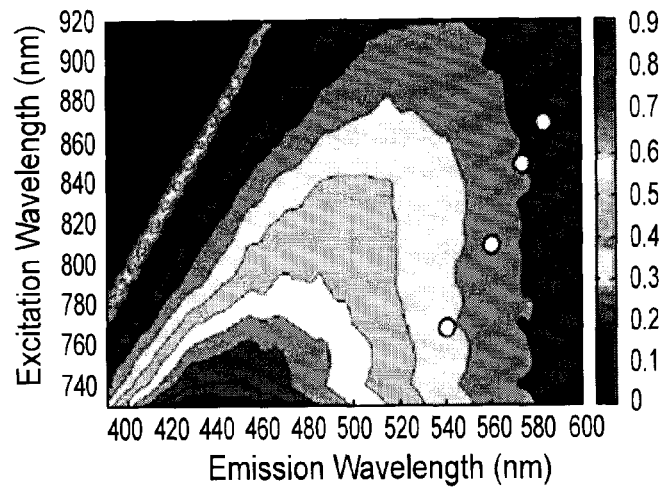
FIG. 29(A) to (C) are EEM plots of pure collagen obtained with a multiphoton microscopy assembly according to an embodiment of the invention.
Figure 29B:
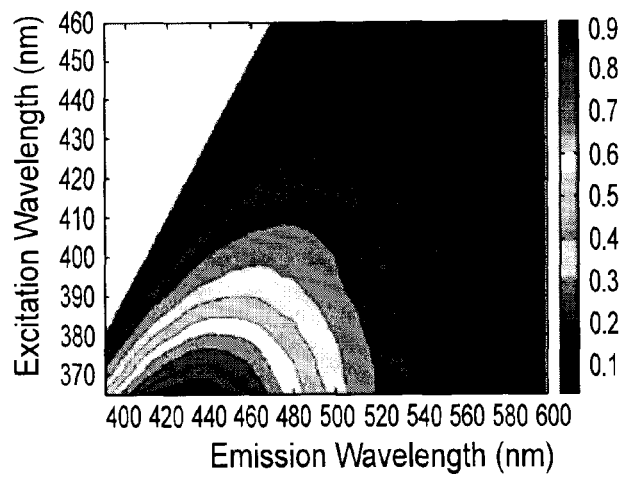
Figure 29C:
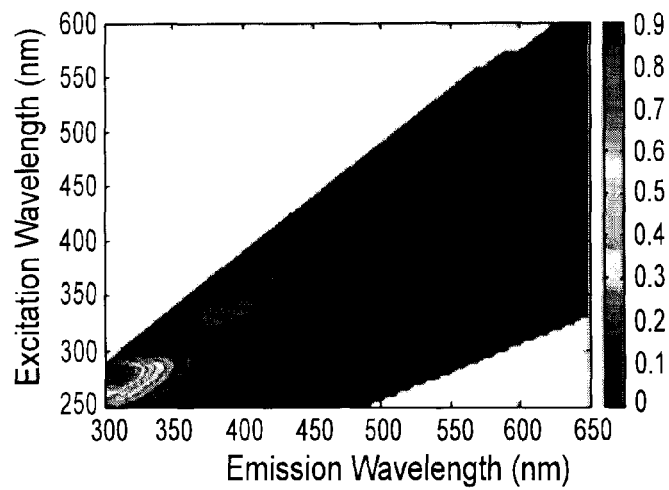

FIGS. 29A to 29C show EEM results of a purified human collagen sample (Type I). The collagen sample (HS150 Collagen Type I, Acid soluble, from human skin, Elastin Products Co. Inc.) was supplied as a white sponge-like material and stored at 4° C. until used for EEM measurements. The collagen was placed between a microscope slide and a piece of cover glass. FIGS. 29A and 29B show two-photon (730 nm to 920 nm) and single-photon (365 nm to 460 nm) EEMs respectively. As seen in FIG. 29A, there are a series of narrow peaks in addition to a TPF signal. These narrow peaks originate from SHG emission from the purified collagen because the emission wavelengths of those peaks are exactly half of the corresponding excitation wavelengths. This can be a unique characteristic of collagen fiber. Since single-photon EEM does not have SHG signals, two-photon EEM has better performance in distinguishing the epidermis from the dermis, and elastin fibers from collagen fibers. There are several known excitation emission pairs for TPF of pure human skin collagen Type I (HS150, Elastin Products Co. Inc.) including: (770 nm, 472.5 nm), (810 nm, 487.6 nm), (850 nm, 503.0 nm) and (870 nm, 512.9 nm), which are shown by the white circles in FIG. 29A. The known results shows agreement with the TPF part in the present EEM measurement results in FIG. 29A. Single-photon EEM with an excitation range from 250 nm to 600 nm is shown in FIG. 29C, which indicates that the major peaks for single-photon fluorescence from human keratin are located in the UV excitation range.

Figure 27A:
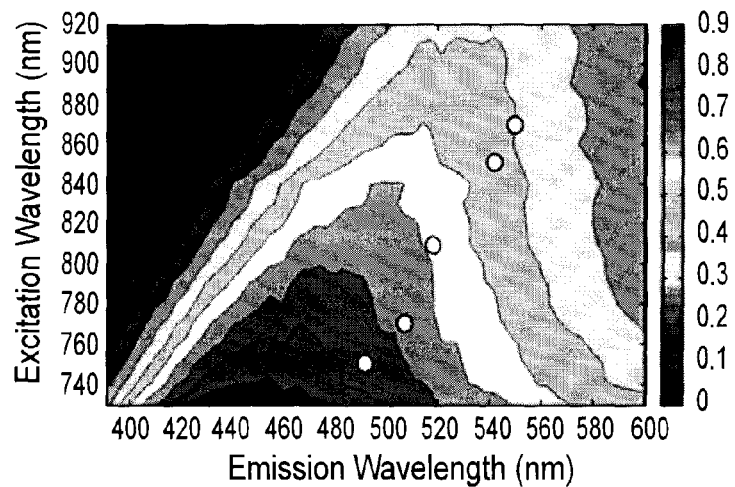
FIG. 27(A) to (C) are excitation-emission matrix (EEM) plots of purified elastin obtained with a multiphoton microscopy assembly according to an embodiment of the invention.
Figure 27B:
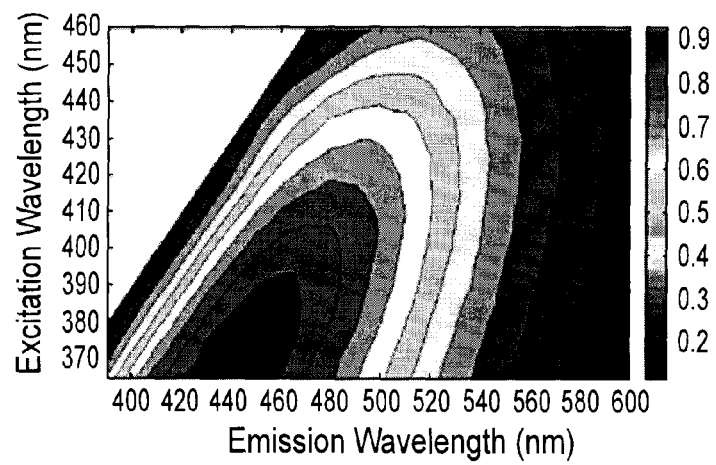
Figure 27C:
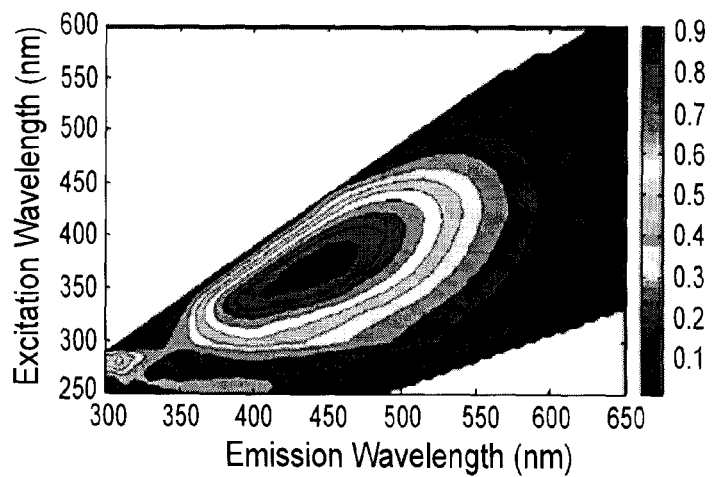

FIGS. 27A and 27B are two-photon and single-photon EEM results respectively with the same range of excitation wavelengths. In the single-photon EEM, the maximum excitation emission pair was at (375 nm, 450 nm), while the maximum excitation emission pair was at (~730 nm, ~460 nm) for two-photon EEM. Maximum fluorescence occurred at similar emission wavelengths for single-photon and two-photon EEM, and the two EEMs have similar patterns over the whole range. As expected, the excitation wavelengths in two-photon EEM were roughly two times that of single-photon EEM. This comparison shows similarities and differences between two-photon and single-photon EEM. Purified elastin sample is known to show TPF excitation-emission-pairs at (750 nm, 457.9±0.4 nm), (770 nm, 465.5±0.4 nm), (810 nm, 479.8±0.8 nm), (850 nm, 503.0±0.2 nm) and (870 nm, 512.9±0.4 nm), which are shown by the white circles in FIG. 27A. The known results are consistent with the present measurements. Single-photon EEM with an excitation range from 250 nm to 600 nm is shown in FIG. 27C, which exhibits additional peaks in the UV excitation range.

Figure 28A:
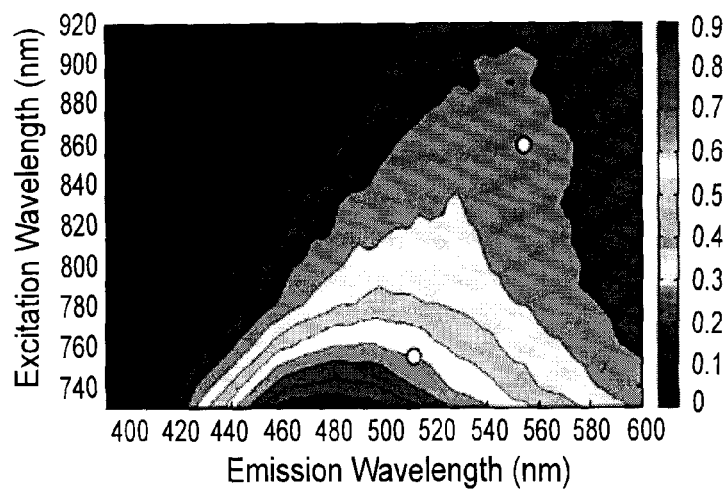
FIG. 28(A) to (C) EEM plots of purified keratin elastin obtained with a multiphoton microscopy assembly according to an embodiment of the invention.
Figure 28B:
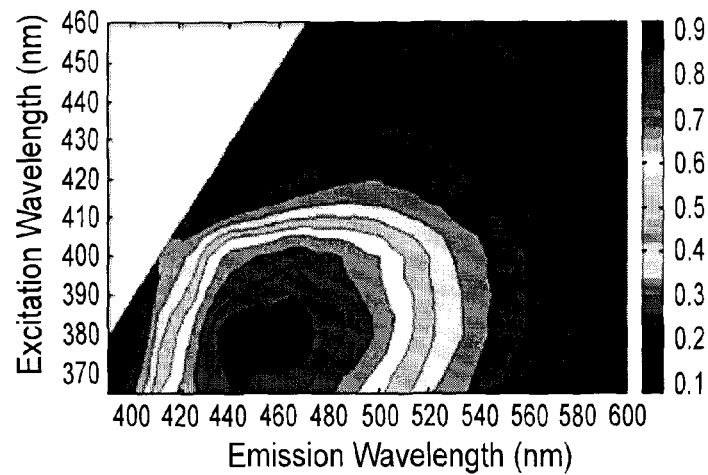
Figure 28C:
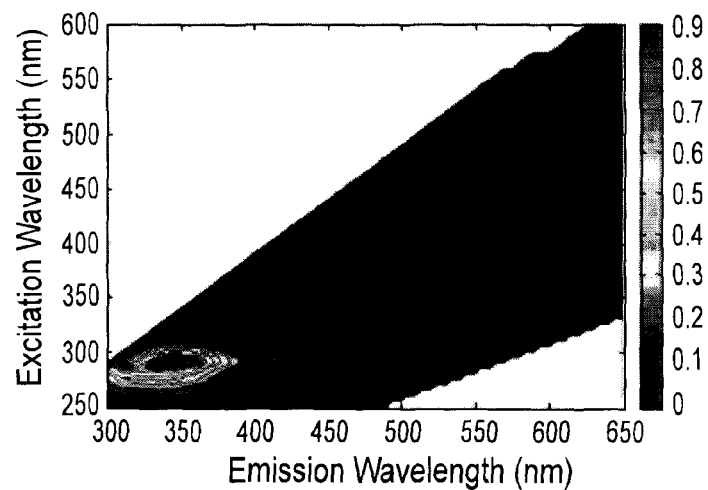

FIGS. 28A to 28C are EEM results of purified human keratin (Product K0253, Sigma Aldrich, 1 mg/ml solution in urea) from human epidermis. 30 ml of the keratin solution was placed in a central depression of a flat plastic vessel. A piece of cover glass was placed over the depression. Single-photon and two-photon EEM results have different patterns and different maximum excitation-emission pairs because two-photon and single-photon fluorescence have different absorption coefficients which result from various selection rules for the transition of electronic states of the fluorophore molecules.

FIG. 28A shows two-photon EEM results obtained with an excitation wavelength range of 730 nm to 920 nm, at a power of 30 mW and an exposure time of 2 seconds. FIG. 28B shows one-photon EEM results obtained with an excitation wavelength range of 365 nm to 460 nm. The maximum excitation emission pair is at (~380 nm, ~450 nm) for single-photon EEM (FIG. 28B), while it is at (~730 nm, ~475 nm) for two-photon EEM (FIG. 28A). Due to the limit of scanning range, data was not acquired for excitation wavelengths below 730 nm. In FIG. 28A there are two excitation emission pairs at (760 nm, 490 nm) and (860 nm, 530 nm). These results match with reported results of (760 nm, 475±5 nm) and (860 nm, 515±5 nm), which are shown as the two white circles on the EEM plot, for pure human keratin (K0253, Sigma Aldrich, 30 mg/ml solution in urea). Single-photon EEM with an excitation range from 250 nm to 600 nm is shown in FIG. 28C.

FIGS. 29A to 29C show EEM results of a purified human collagen sample (Type I). The collagen sample (HS150 Collagen Type I, Acid soluble, from human skin, Elastin Products Co. Inc.) was supplied as a white sponge-like material and stored at 4° C. until used for EEM measurements. The collagen was placed between a microscope slide and a piece of cover glass. FIGS. 29A and 29B show two-photon (730 nm to 920 nm) and single-photon (365 nm to 460 nm) EEMs respectively. As seen in FIG. 29A, there are a series of narrow peaks in addition to a TPF signal. These narrow peaks originate from SHG emission from the purified collagen because the emission wavelengths of those peaks are exactly half of the corresponding excitation wavelengths. This can be a unique characteristic of collagen fiber. Since single-photon EEM does not have SHG signals, two-photon EEM has better performance in distinguishing the epidermis from the dermis, and elastin fibers from collagen fibers. There are several known excitation emission pairs for TPF of pure human skin collagen Type I (HS150, Elastin Products Co. Inc.) including: (770 nm, 472.5 nm), (810 nm, 487.6 nm), (850 nm, 503.0 nm) and (870 nm, 512.9 nm), which are shown by the white circles in FIG. 29A. The known results shows agreement with the TPF part in the present EEM measurement results in FIG. 29A. Single-photon EEM with an excitation range from 250 nm to 600 nm is shown in FIG. 29C, which indicates that the major peaks for single-photon fluorescence from human keratin are located in the UV excitation range.

Figure 30:
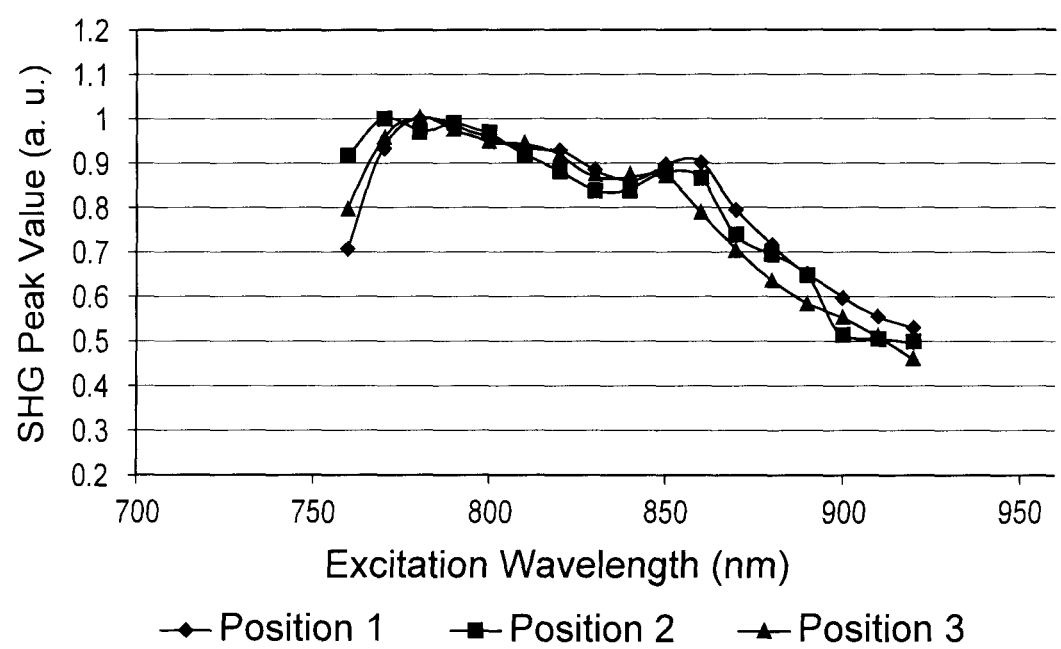
FIG. 30 is a graph showing excitation of SHG signals from human collagen detected using a multiphoton microscopy assembly according to an embodiment of the invention.

The excitation spectrum of the SHG signal (peak value of SHG emission spectrum vs. excitation wavelength) can provide suggestions on choosing the optimal laser wavelength for two-photon analysis of tissues rich in collagen fibers. FIG. 30 shows three different SHG excitation spectra measured from three different locations on the purified human collagen sample with an excitation wavelength range of 730 nm-920 nm, 20 mW excitation power, and three second exposure time. These excitation spectra show a major peak at ~790 nm and a secondary peak at ~850 nm. These results match to a certain extent with known results which show a major peak at ~810 nm and a secondary peak at ~850 nm.

Figure 31A:
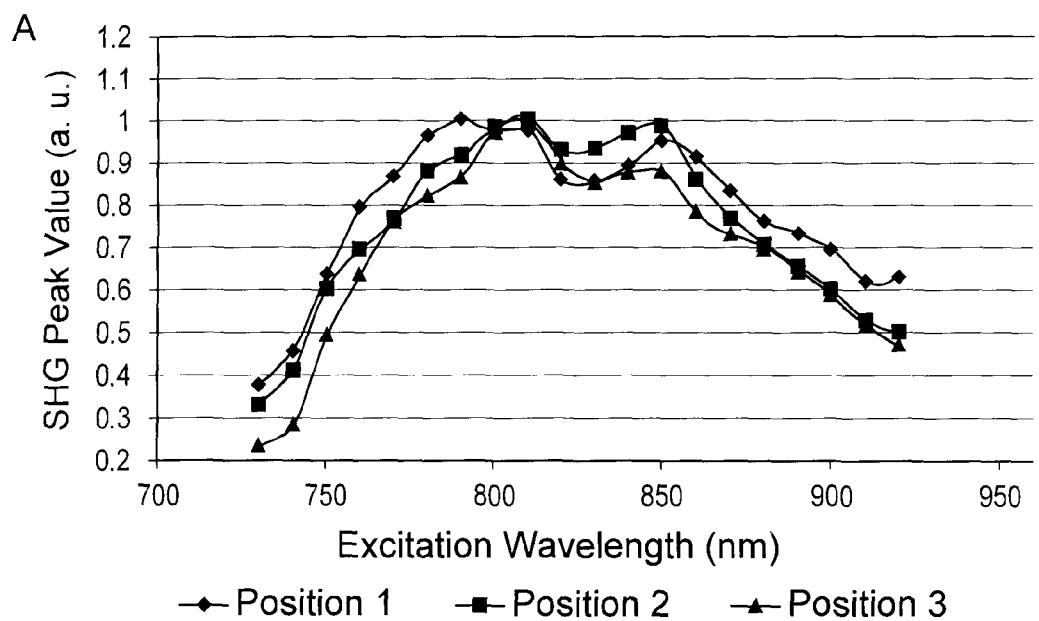
FIGS. 31A and 31B are graphs showing excitation of SHG signals from collagen from fish scale and rat tail tendon, respectively, detected using a multiphoton microscopy assembly according to an embodiment of the invention.
Figure 31B:
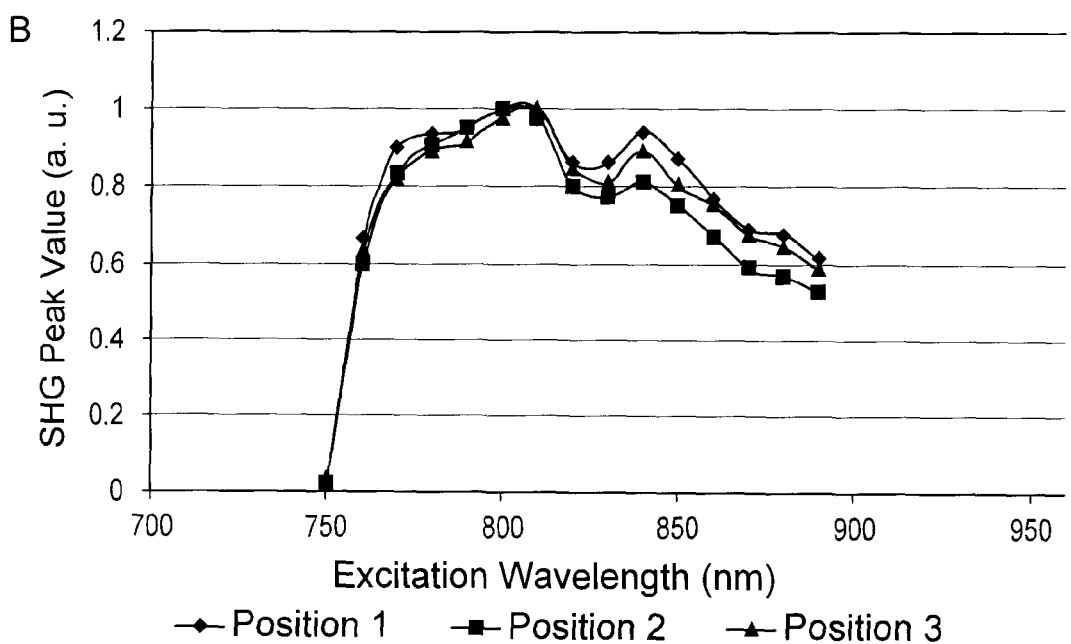

SHG excitation spectra of other collagen samples were also measured. Samples included fish scale and rat tail tendon, which are rich in collagen fibers (FIGS. 31A and 31B). Comparing the excitation spectra in FIGS. 30 and 31, different samples show different spectral characteristics in terms of peak positions and width of spectrum. These characteristics may be related to structure and chemical characteristics of collagen fibers, which are important for complex tissue analysis.

Other important endogenous fluorophores for two-photon study of skin include NADH, FAD, and melanin. NADH and FAD are significantly involved in cell metabolism activities. Melanin is an excellent photoprotectant for skin.

Figure 32A:
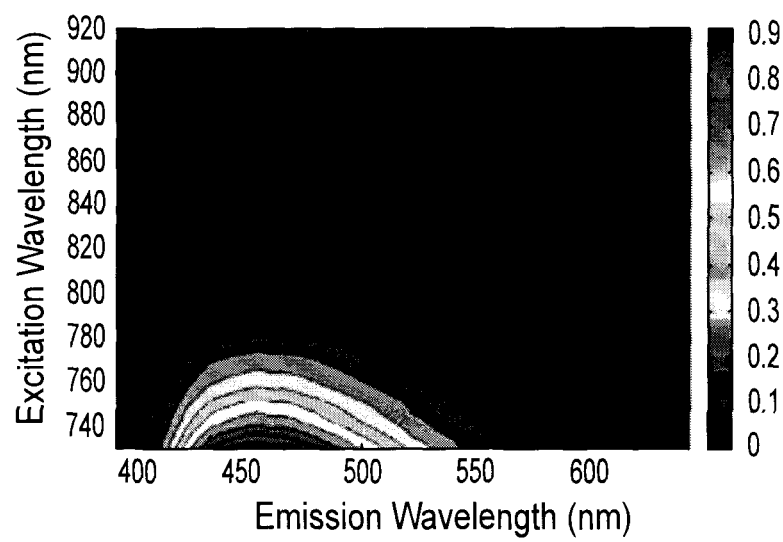
FIGS. 32A to 32D are EEM plots of various fluorophores obtained with a multiphoton microscopy assembly according to an embodiment of the invention.
Figure 32B:
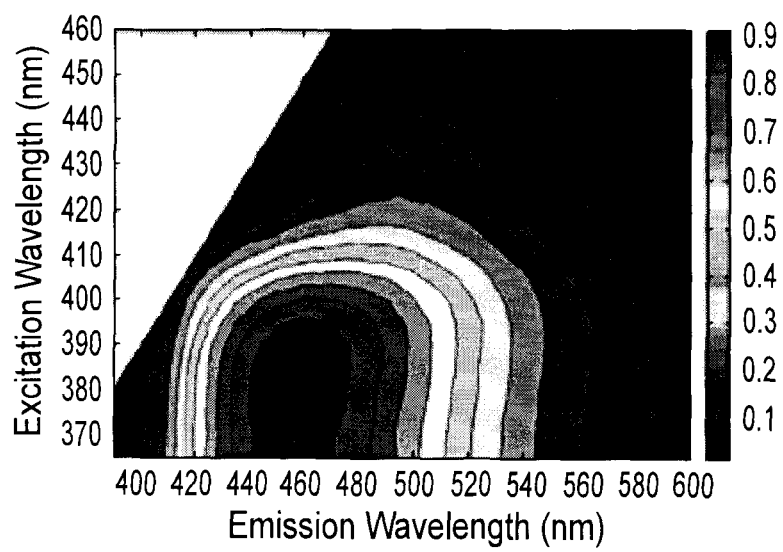
Figure 32C:
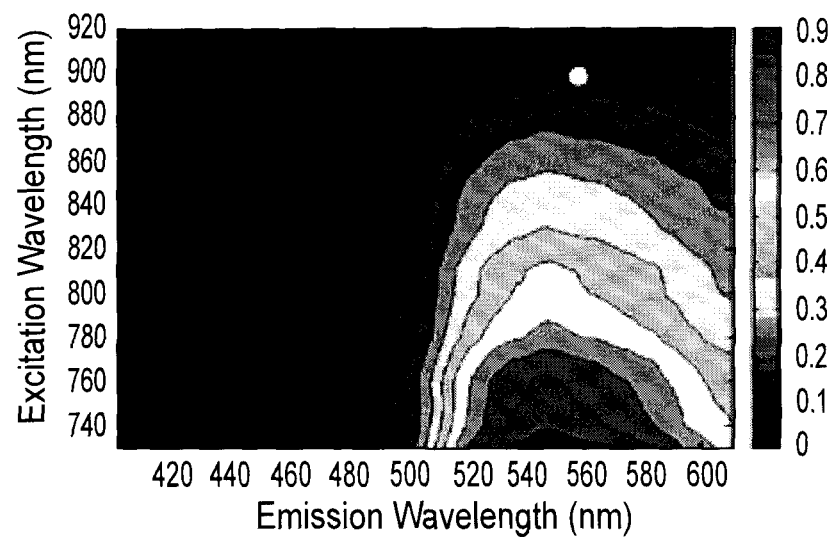
Figure 32D:
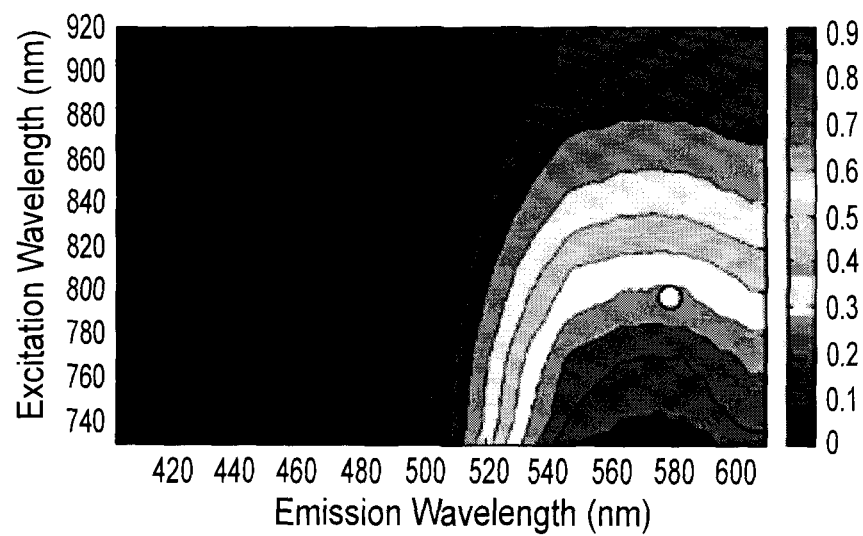

Purified NADH (N6879-25MG, α-Nicotinamide adenine dinucleotide, reduced disodium salt, Analog of β-NADH, chemically reduced, Sigma Aldrich) and FAD (F6625-10MG, Flavin adenine dinucleotide disodium salt hydrate, Sigma Aldrich) in powder form were placed between a microscope slide and cover glass for analysis. Melanin powder (M8631-250MG, Sigma Aldrich) was dissolved in 1 mol/l $NH_4OH$ to provide a 1 mg/mL solution. EEM of the melanin solution was measured in the same way as the keratin solution discussed above. Two-photon EEMs of NADH, FAD and melanin are summarized in FIGS. 32A, 32C and 32D respectively. FIG. 32B shows a one-photon EEM of NADH. Excitation wavelengths of 730 nm to 920 nm, an excitation power of 20 mW, and an exposure time of three seconds were used. The excitation-emission pairs in the EEMs of FIG. 32B show agreement with the reported results as: (730 nm, 545 nm) and (900 nm, 540 nm) for FAD (solution, Sigma Aldrich), (800 nm, 565 nm) for melanin (Synthetic melanin prepared by oxidation of tyrosine with hydrogen peroxide, solution in KOH, Sigma Aldrich), and (730 nm, 460 nm) for NADH (solution, Sigma Aldrich). FIGS. 32A, 32C and 32D indicate these known results as white circles on the contour map.

The nonlinear EEM for each purified fluorophore measured above has a distinct pattern and serves as useful signatures for characterization of complex skin tissues. In some embodiments, the multiphoton microscopy assemblies of the invention may include a processor that uses these signatures to putatively identify biological structures and/or biological activities in a sample.

Experiments on Normal Human Skin Tissue

Figure 33C:
FIG. 33C is an EEM plot of same obtained using a multiphoton microscopy assembly according to an embodiment of the invention.
Figure 33C:
Figure 33C:
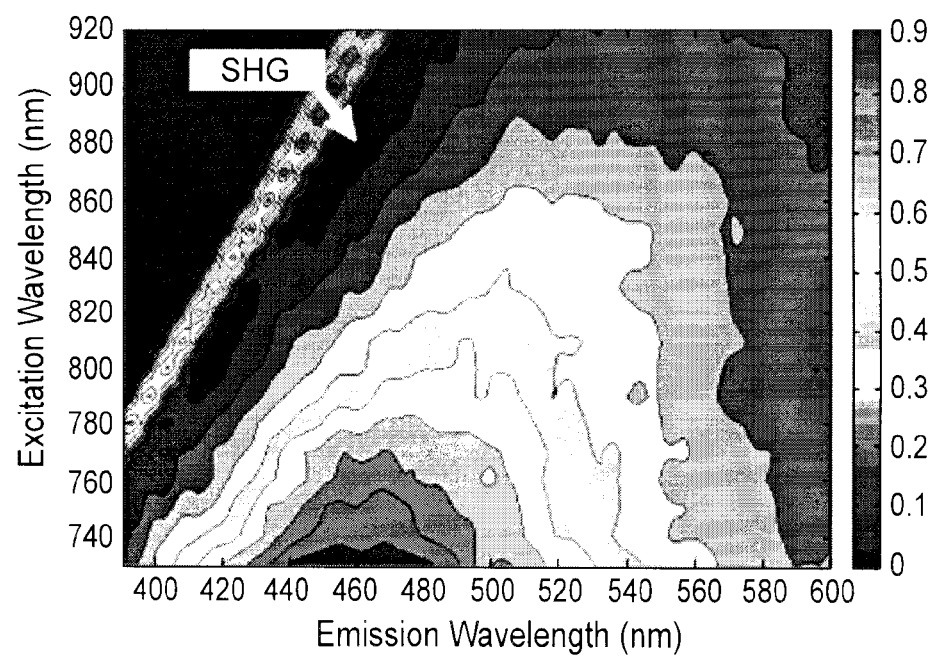

Fresh normal skin (~2 mm thickness, ~1 cm×1 cm area) excised from a human temple without sectioning was subject to EEM measurement within 1 hour after excision using a multiphoton microscopy assembly according to an example embodiment of the invention. After all EEM measurements were completed, the tissue was fixed in formalin and processed by H & E staining for histological image acquisition. FIG. 33A is a combined TPF/SHG/confocal image of a cross section view of the epidermis-dermis junction in a field of view of 100 μm×100 μm. FIG. 33B is a H&E stained histology image of a similar region, wherein the box represents an area of 100 μm×100 μm which matches with the field of view in FIG. 33A. A papillary structure can be seen in both FIGS. 33A and 33B, which is a typical structure at the epidermis-dermis junction. FIG. 33C is an EEM for this cross-section showing two parts, namely wide TPF curves and a narrow SHG peak array. The emitted SHG peak is located at half of the excitation wavelength, and originates from collagen fibers. The TPF portion of the EEM has a similar pattern and excitation-emission-pairs as the pure elastin sample; however, it is shifted a little to the longer wavelength side, which may be due to contribution of emission from keratin from epidermal cells.

Five distinct layers were measured in the vertical direction from the stratum corneum to the dermis layer. FIGS. 34A to 34E each show 50-image-averaged images of: four sub-layers of the epidermis compartment and one layer from the dermis compartment, respectively. For the epidermis compartment the TPF channel was mainly used for the imaging guidance purpose. Imaging depths of the four epidermal sub-layers were: 10 μm, 20 μm, 30 μm and 40 μm (FIGS. 34A to 34D respectively). The other layer with an imaging depth of 60 μm was the dermis compartment (FIG. 34E). The field of view for these images is 100 μm×100 μm and the scale bar in the Figures is 20 μm. All images were taken using an excitation wavelength of 790 nm and excitation power of 30 mW.

Figure 34A:
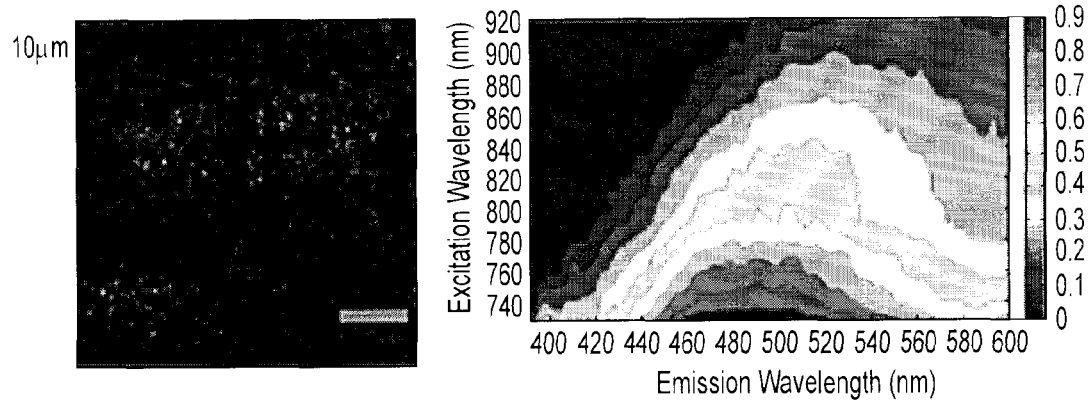
FIGS. 34A to 34E are images and EEM plots of normal skin obtained using a multiphoton microscopy assembly according to an embodiment of the invention.
Figure 34B:
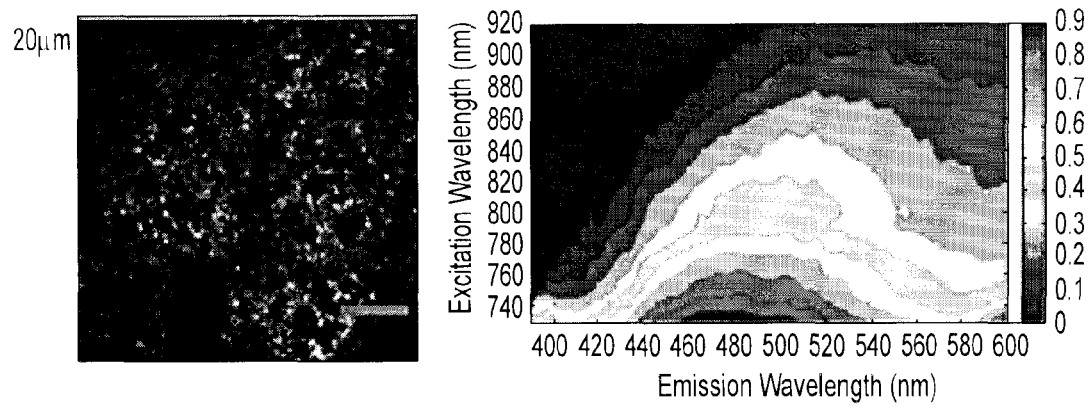
Figure 34C:
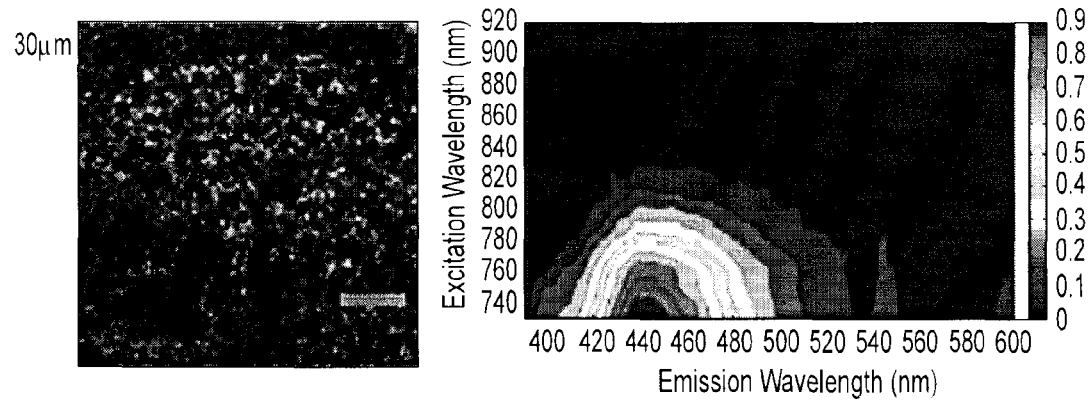
Figure 34D:
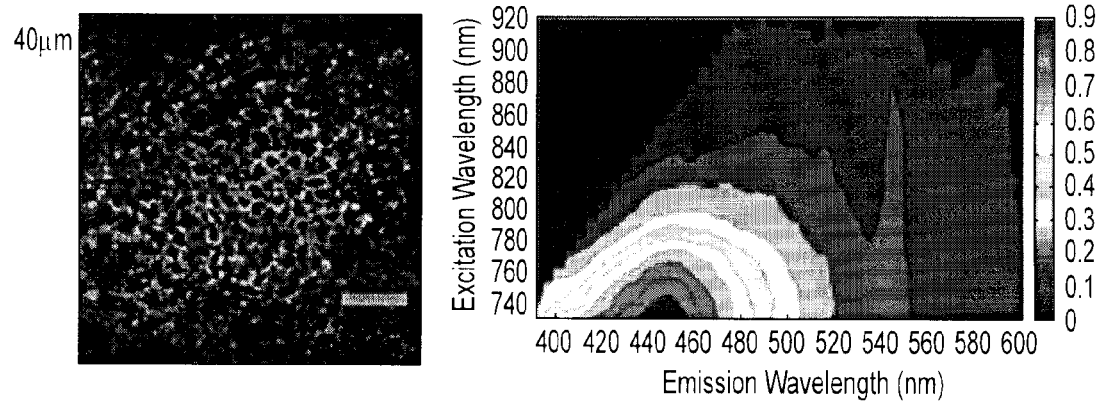
Figure 34E:
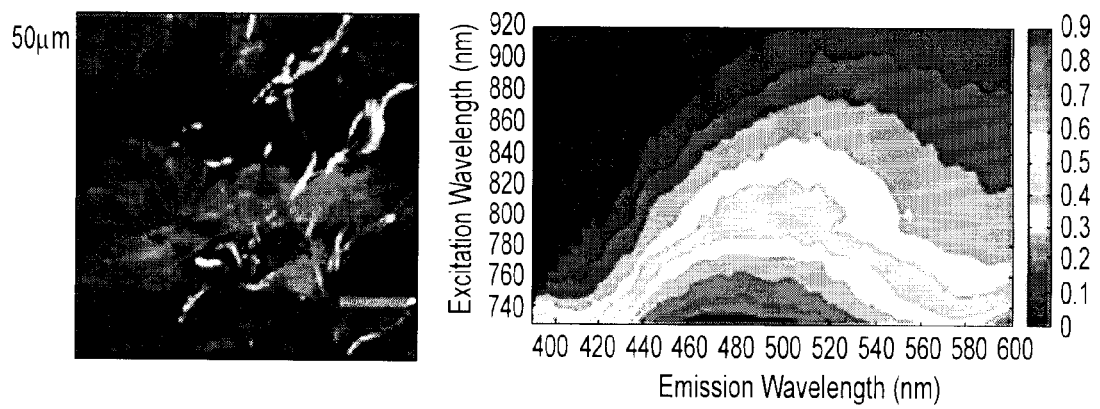

As seen in FIG. 34A, stratum corneum cells have large sizes. The EEM maximum excitation emission pair is located at (730 nm, 470 nm), which is close to that of purified keratin as in our previous measurement (730 nm, 480 nm). Imaging deeper, the number of cells increases while the size of cells decreases. EEMs for the first two sub-layers (FIGS. 34A and 34B) indicate that most of the TPF signals in these layers come from keratin, which mainly exists at the surface of skin. For the third and fourth sub-layers (FIGS. 34C and 34D), the stratum spinosum and stratum basale, the EEMs have the pattern and the maximum excitation emission pairs resembling that of pure NADH, indicating most of the TPF signal in these layers originates from NADH. NADH is significantly involved in redox reactions for metabolism, hence these EEMs show that cells are more active in the stratum spinosum and stratum basale layers. This is consistent with known skin biology—because cells in the epidermis originate from the stratum basale layer and keep proliferating and migrating to the top layers, cells at a deeper layer are more metabolically active.

FIG. 34E shows an averaged image and EEM data for one layer in the dermis compartment. The SHG channel was added and optimized for this layer for image-guidance purpose. The dotted array in the EEM plot comprises SHG peaks with each emission peak located at exactly half of the excitation wavelength respectively. The SHG signal originates from collagen fiber in the dermis layer. The peaks with larger bandwidths represent the TPF signal. The TPF part of this EEM has a similar major excitation emission pair (730 nm, 450 nm) and overall pattern as pure elastin. Signals acquired in the imaging channels supports this analysis. The TPF imaging channel mainly showed thin elastic fiber structures while the fiber bundle structure of collagen was only observed in the SHG imaging channel. There was no overlap between SHG and TPF signals, which indicates that collagen fiber in fresh skin tissue does not have strong TPF emission at 790 nm excitation. SHG intensity in this EEM plot is attenuated 20 times so that the contour details of SHG and TPF signal can be displayed on a single plot. The SHG/TPF ratio for purified collagen is different from that of collagen fibers in skin tissue, which may be due to the purification process changing the structure of collagen.

Experiments on Human Skin Tissue with Seborrheic Keratosis (SK)

Figure 35A:
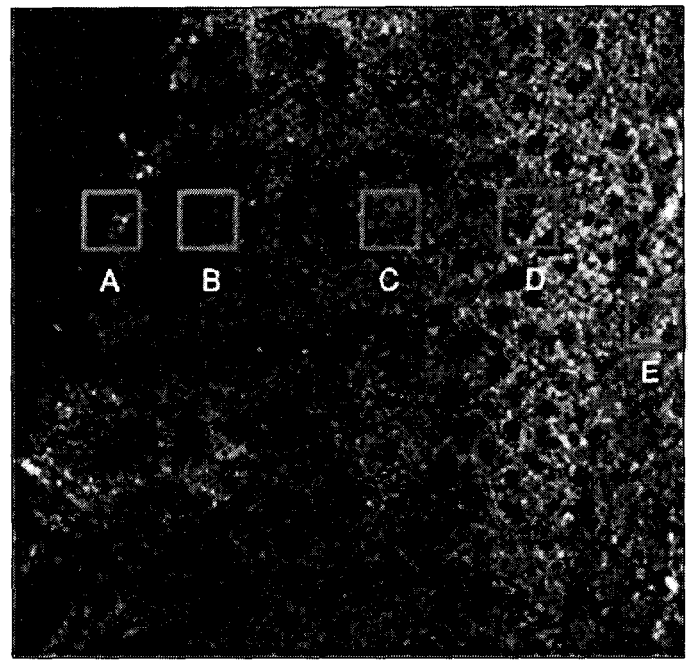
FIGS. 35A and 35B are an image of skin with seborrheic keratosis taken using a multiphoton microscopy assembly according to an embodiment of the invention, and an H&E stained sample of same, respectively.
Figure 35B:
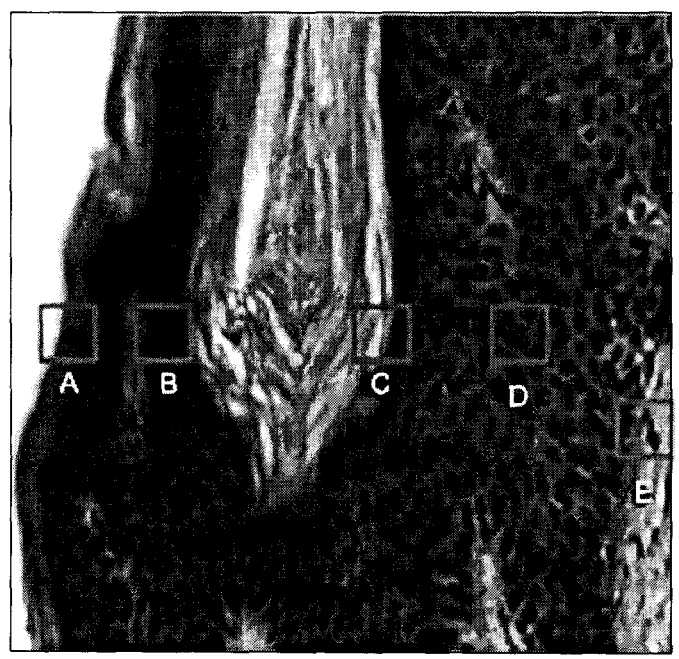

Diseased human skin tissue with SK was also investigated for comparison with normal skin tissue EEM. This type of tissue usually has histological characteristics such as basal cells mixed with squamous cells and keratin-filled invaginations of the epithelium. FIG. 35A is a TPF/SHG image (acquired using a multiphoton microscopy assembly according to an example embodiment of the invention) and FIG. 35B is an H&E stained histological image of the same sample of a transverse slice of human shoulder skin with SK with a field of view of 200 μm×200 μm. The dimension of the boxes in the images are 20 μm×20 μm. An excitation wavelength of 790 nm and excitation power of 30 mW was used.

Figure 36A:
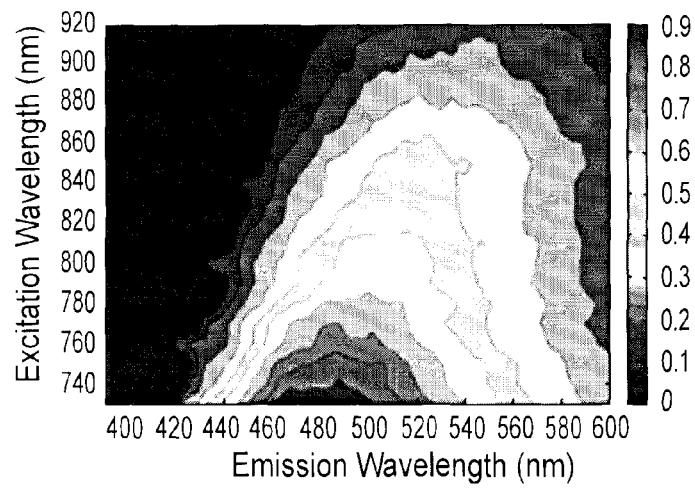
FIG. 36A to 36E are EEM plots of skin with seborrheic keratosis obtained using a multiphoton microscopy assembly according to an embodiment of the invention.
Figure 36B:
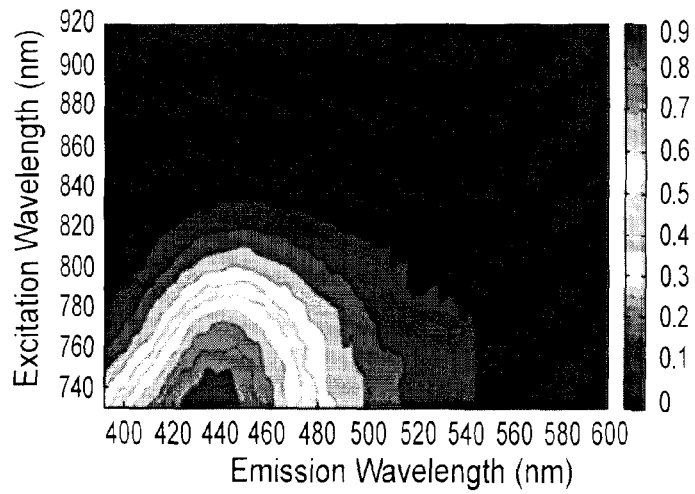
Figure 36C:
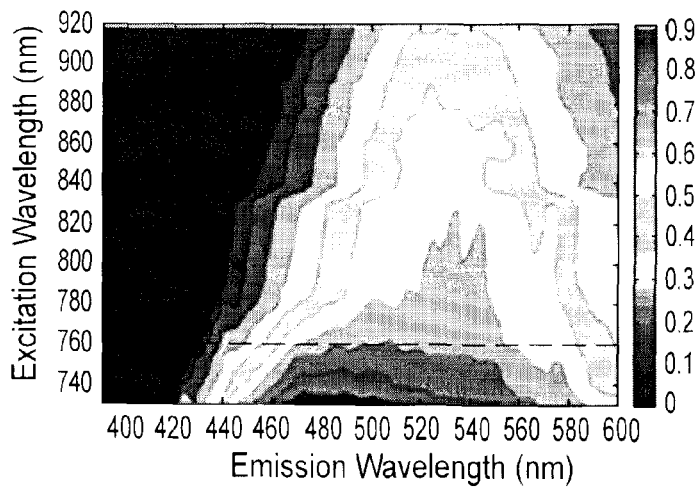
Figure 36D:
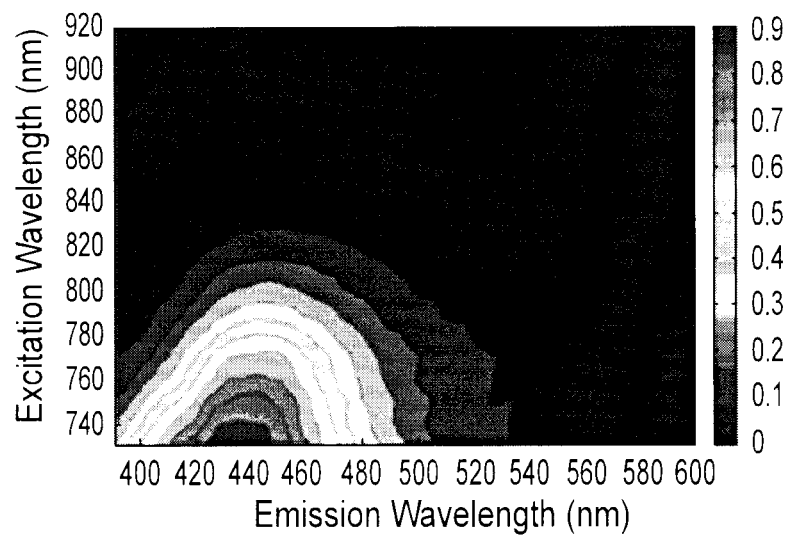

FIGS. 36A to 36E show EEMs acquired from the five square areas indicated by the squares labelled A to E in FIGS. 35A and 35B. Excitation wavelengths of 730 nm to 920 nm, excitation power of 30 mW, and exposure time of two seconds was used. In FIG. 36A, the EEM has a similar pattern and maximum excitation-emission-pair as that of pure keratin sample. FIG. 36A corresponds to square A in FIG. 35B where the keratin structure can be observed clearly in the histological image. In FIGS. 36B and 36D, both of the EEMs resemble that of pure NADH, which is consistent with the cellular structures as highlighted by the squares B and D in FIG. 35.

Figure 36E:
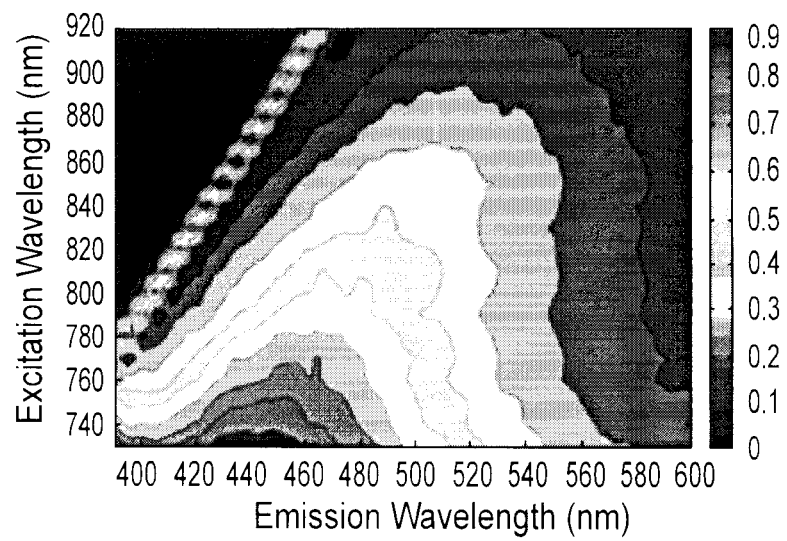

In FIG. 36C, the EEM seems to be a mixture of signals originating from various structures. The contour pattern and excitation-emission pairs below excitation of 760 nm (black dotted line) are similar to pure keratin, while the pattern above 760 nm shows similarity with that of purified FAD sample. This spectral characteristic is consistent with the image signal in square C on FIG. 35B, which includes both keratin and cellular structures in it. This analysis shows the advantage of EEM compared with pure emission spectra or excitation spectra, since this tissue characteristic cannot be fully revealed using only one excitation wavelength or one emission wavelength. More importantly, EEM reveals the fact that a keratin structure has intruded into the middle sub-layers of the epidermis part of this SK tissue sample. This result is consistent with the biological characteristic of SK tissues, and demonstrates the applicability of image-guided EEM for diagnosis of skin diseases. FIG. 36E shows the EEM for the last square E which is located in the dermis layer mainly containing fiber structures. The dotted array is related to SHG peaks from purified collagen. The TPF spectra have a contour pattern similar to purified elastin fiber.

Comparing the results from normal skin tissue with the results from SK skin tissue, EEMs show different characteristics at certain layers and show consistency with the biological characteristics of both tissue types. The results indicate imaging-guided nonlinear EEM can be advantageously used for skin disease diagnosis.

Multiphoton Absorption Photothermolysis

Multiphoton microscopy assemblies according to some embodiments of the invention may be used to target a microstructure by multiphoton image visualization and/or spectral analysis, and then damage or destroy the target by scanning and focusing a high intensity laser beam within the target.

Figure 37:
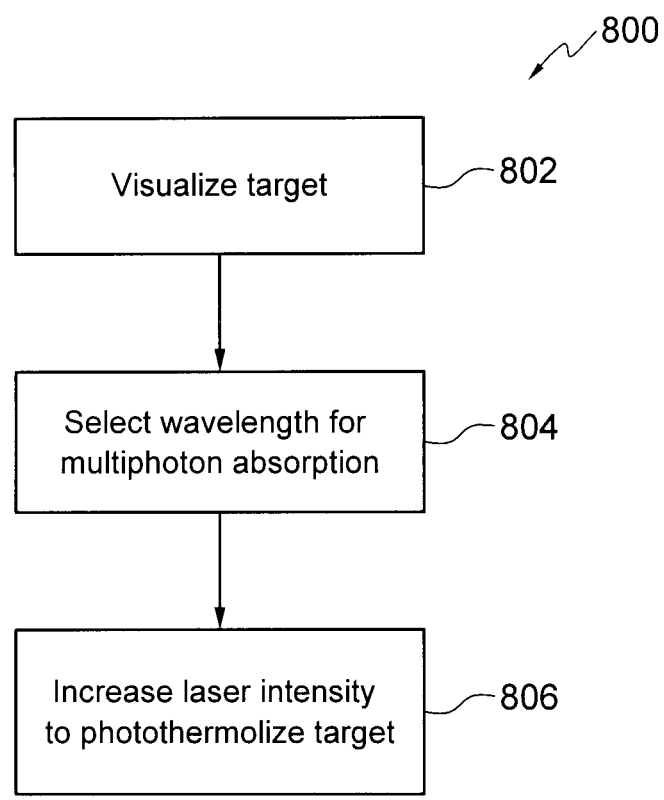
FIG. 37 is a block diagram illustrating a photothermolysis method according to an embodiment of the invention.

A photothermolysis method 800 according to an embodiment of the invention is illustrated in FIG. 37. At box 802, the region of interest is visualized using the imaging techniques described above, such as through use of multiphoton microscopy assemblies of the invention including assemblies 100 and 200. At box 804, the wavelength may be chosen so that strong multiphoton (e.g. two photon) absorption will be generated by the target and generate localized heat to destroy the target. At box 806, the laser intensity may be chosen so that the target is damaged or destroyed. In some embodiments, the intensity of the laser beam at the target may be at least 75 mW when a wavelength of 785 nm is used. Other embodiments may use other suitable intensities and wavelengths depending on the target region. Because the multiphoton absorption will occur only at the focal point and not on other locations along the light path where light intensity is lower, other tissue components (even those having the same or stronger absorption properties as the target) will not be affected or damaged.

Since proteins and DNA have strong absorption in UV wavelength ranges, almost any types of microstructures in tissue could be targeted by an appropriate laser beam in the red to near infrared wavelength ranges. According to some embodiments of the invention, precise microsurgery of any microstructures of interest can be carried out by combining multiphoton microscopic image targeting and multiphoton absorption photothermolysis.

In some embodiments, dark or black hair follicles and shafts in dark or black skin can be targeted microscopically and destroyed by laser without affecting the surrounding skin tissue even though the surrounding skin may contain high concentrations of light absorbing melanin.

In some embodiments, cancer cells (e.g. melanoma cells) can be visualized and differentiated from benign or normal cells and then destroyed by a high intensity laser beam. Tumor destruction may for example be on a cell-by-cell basis. For high efficiency, a cancer cell cluster (e.g. basal cell island in basal cell carcinomas) may also be destroyed at one time. In some embodiments, cancer stem cells can be identified and destroyed.

In some embodiments, vascular skin lesions may be treated by selectively destroying excessive blood vessels. A certain number of vessels may be maintained for normal physiological functions of the tissue.

In other embodiments, one or more of the following conditions may be visualized and treated: oral disorders such as oral lesions and oral cancers; nail fungus and other nail and hair disorders; ophthalmic disorders and eye diseases like glaucoma; internal lesions and disorders that become accessible during surgery (e.g. brain tumors and Parkinson's disease, during neural surgery).

In some embodiments, the invention can be used in endoscopic applications for both diagnosis and therapy at microscopic accuracy. The present invention provides access to internal organs through an endoscope by fiber delivery of the laser light and use of a miniaturized scanner.

In some embodiments, the invention can be used for wrinkle removal and skin resurfacing by targeting skin collagen with multiphoton (e.g. two-photon) absorption.

In some embodiments, the invention can be used for subcutaneous fat removal by targeting adipose cells with multiphoton (e.g. two-photon) absorption.

In some embodiments, the invention can be used for tooth whitening by removing microscopic surface pigments.

In some embodiments, cosmetic blemishes of the skin such as scars, birthmarks, hyperpigmented or hypopigmented regions, and/or unwanted tattoos may be removed through microscopically targeted multiphoton absorption photothermolysis. Removal may be accomplished without damage to neighboring regions of skin. Some pigmented tattoo particles are difficult to remove with current conventional one-photon photothermolysis. Multiphoton (e.g. two photon) absorption photothermolysis enables focused ablation of such particles.

Clinical Use Example

The multiphoton microscope assemblies of the invention such as assemblies 100 and 200 may be employed as follows in a clinical setting.

A patient seeks a consultation with a user (e.g. a dermatologist) regarding a large and irregular mole on the back of the patient's hand. The user determines through a naked eye visual inspection of the mole that further investigation is indicated in order to make a proper diagnosis. Instead of performing a biopsy, the user visualizes the micromorphology of the patient's mole using a multiphoton microscope assembly according to an embodiment of the invention.

The patient is seated and his hand placed palm down on an examination stand in a resting position. The user request the patient to keep his hand as still as possible. An adapter with a bore greater than the area of the mole is attached around the mole with a quick curing non-permanent adhesive. Once the adhesive has cured, the adapter is filled with a suitable objective immersion medium. As the base of the translation stage of the multiphoton microscope assembly is coupled to the adapter, the objective mounted to the table of the translation stage is immersed in the immersion medium. Multimodal imaging is commenced for real time viewing of the mole.

The user moves the objective by using controls on the assembly which control the motorized translation stage. The controls on the assembly may be physical dials, knobs, buttons and the like, or controls displayed a graphical user interface operated by touch screen, keyboard, joystick, mouse and the like. The position of the table of the translation stage is adjusted in three dimensions to position the objective in the desired position for viewing.

The user may operate:
excitation wavelength controls on the assembly to adjust the excitation wavelength in real time to optimize the strength of the multiphoton signal(s) being detected;
field of view controls on the assembly to adjust the field of view;
excitation power controls on the assembly to adjust the excitation power (by adjusting the attenuator motor). Additional controls may be provided to allow the user to set a predetermined or user-defined constant level of excitation power.

The user may also switch to an "automatic detection mode" of the assembly to automatically identify on the assembly's display various common endogenous fluorophores (e.g. elastin, collagen, keratin, melanin, NADH, FAD, etc.) by instructing a processor to compare preloaded, known fluorescence/spectroscopic signatures with detected multiphoton and spectroscopic signals of structures in the field of view. Identification on the assembly's display could for example be manifested by false colour overlaid images of two or more fluorophores, or separate images of one specific fluorophore at a time. Based on the parameters such as density and distribution of these fluorophores the user can determine whether the structures in the field of view are, for example, normal or abnormal, benign or cancerous, etc. This determination may also be performed automatically by a processor in the assembly by comparing the detected density and/or distribution of particular fluorophores with known densities and/or distributions for particular conditions. The automatic determination may for example also factor in other inputted factors such as imaging depth, body location, age and sex of the subject, etc.

If an imaged region within the mole is determined to be normal or benign, the user moves the translation stage to image another structure. If the imaged region is determined to be cancerous, the user may upon obtaining the patient's consent proceed with photothermolysis of the cancerous region. The user adjusts the appropriate controls (e.g. laser power control, wavelength control) to suitable levels for photothermolysis. After ablating the cancerous region with high intensity laser, the user adjusts the controls back to a levels suitable for imaging to confirm the cancerous region has been destroyed or adequately damaged.

As will be apparent to those skilled in the art in the light of the foregoing disclosure, many alterations and modifications are possible in the practice of this invention without departing from the spirit or scope thereof. For example: software may be provided to (1) coordinate operation of the described assemblies with one or more of the described measurement modes (e.g. MPM imaging, RCM imaging, spectral measurements) and/or (2) provide a variable scanning speed, and therefore variable imaging frame rate; and/or (3) scan a region of interest of any shape to facilitate spectral measurements of the targeting microstructure or for targeted photothermolysis.

1. diseases or physiological states may be diagnosed by detection and/or measurement of the fluorescence or spectra (e.g. Raman spectra) of subsurface blood vessels in a non-invasive manner.
2. glucose levels in subsurface blood vessels may be determined by measurement of fluorescence or spectra (e.g. Raman spectra) in a non-invasive manner.
3. drug localization and drug concentration may be determined by the detection and/or measurement of the fluorescence and/or spectra of such drugs, and/or drug breakdown products (metabolites), and/or compounds having concentrations affected by a drug, in targeted microstructures such as blood or skin.
4. miniaturization of the described technologies utilizing MEMS (micro-electro-mechanical system), MOEMS (micro-opto-electro-mechanical system) technologies, and/or nanotechnologies.

What is claimed is:

1. A microscope comprising:
an excitation source operable to emit an optical excitation beam at an excitation wavelength $\lambda$;
a scanner operable to scan the excitation beam on a sample;
an objective arranged to receive the excitation beam output by the scanner, irradiate the sample with the excitation beam scanned by the scanner and collect an emission beam from the sample;
a first detector operable to detect one or more multiphoton signals in the emission beam, the multiphoton signals arising from multiphoton processes in the sample and a second detector operable to detect a confocal reflectance signal in the emission beam;
an emission light path comprising a first wavelength separator operable to separate the emission beam into a first part comprising the one or more multiphoton signals and a second part comprising the confocal reflectance signal, the first wavelength separator allowing transmission from the objective to the first detector of a wavelength band limited to greater than or equal to $\lambda/2$ and less than $\lambda$, wherein the one or more multiphoton signals have wavelengths within the wavelength band;
wherein the one or more multiphoton signals comprises a first multiphoton signal and a second multiphoton signal of different types and the confocal reflectance signal detected at the second detector is coregistered with the one or more multiphoton signals detected at the first detector.

2. A microscope according to claim 1 wherein the first multiphoton signal comprises a two photon fluorescence signal.

3. A microscope according to claim 1 wherein the second multiphoton signal comprises a second harmonic generation signal.

4. A microscope according to claim 1 wherein the first wavelength separator comprises a dichroic.

5. A microscope according to claim 1 wherein the first wavelength separator comprises a shortpass filter.

6. A microscope according to claim 1, wherein the scanner comprises a resonant scanner for scanning a fast axis.

7. A microscope according to claim 1, further comprising:
a third detector;
a second wavelength separator between the first wavelength separator and the first detector, the second wavelength separator operable to direct a portion of the first signal to the third detector.

8. A microscope according to claim 1 comprising an excitation power attenuator.

9. A microscope according to claim 1 comprising a frame grabber connected to receive an output from the first detector and to store an image wherein pixels of the image represent an output of the first detector at corresponding locations on the sample.

10. A microscope according to claim 9 comprising a display connected to display images acquired by the frame grabber.

11. A microscope according to claim 9 wherein the frame grabber acquires images at a rate of at least 12 images per second.

12. A microscope according to claim 1 wherein the excitation source is controllable to change the excitation wavelength.

13. A microscope according to claim 12 wherein the excitation wavelength is controllable in the range of at least 720 nm to 950 nm.

14. A microscope according to claim 12 wherein the excitation source comprises a femtosecond laser.

15. A microscope according to claim 12 wherein the excitation wavelength is a red wavelength or an infrared wavelength.

16. A microscope according to claim 15 wherein the first detector is operative to detect light in the visible spectrum.

17. A microscope according to claim 15 wherein the first detector is operative to detect light in the visible and ultraviolet spectrum.

18. A microscope according to claim 15 wherein the emission light path is configured to block infrared light from reaching the first detector and to pass light in the visible and ultraviolet spectrum to the first detector.

19. A photothermolysis method comprising:
(a) visualizing a target structure using a microscope according to claim 1;
(b) operating the excitation light source at a wavelength at which multiphoton absorption will occur within the target structure;
(c) increasing power output of the excitation light source and focusing light from the excitation light source on the target structure to cause heat to be generated within the target structure by multiphoton absorption within the target structure.

20. A photothermolysis method according to claim 19 wherein step (a) comprises visualizing the target with co-registered TPF, SHG and RCM imaging.

21. A photothermolysis method according to claim 19 wherein step (a) comprises spectrally analyzing the target structure.

22. A photothermolysis method according to claim 19 wherein step (c) comprises destroying the target structure.

23. A photothermolysis method according to claim 19 wherein the target structure comprises a hair follicle or hair shaft.

24. A photothermolysis method according to claim 19 wherein the target structure comprises a cancer cell.

25. A photothermolysis method according to claim 19 wherein the target structure comprises a cancer stem cell.

26. A photothermolysis method according to claim 19 wherein the target structure comprises a blood vessel.

27. A photothermolysis method according to claim 19 wherein the target structure comprises skin collagen.

28. A photothermolysis method according to claim 19 wherein the target structure comprises a cosmetic skin blemish.

29. A photothermolysis method according to claim 19 wherein the target structure comprises surface pigments of teeth.

30. A photothermolysis method according to claim 19 wherein the target structure comprises subcutaneous adipose tissue.

31. A photothermolysis method according to claim 19 wherein the excitation wavelength is a red wavelength or an infrared wavelength.

32. A photothermolysis method according to claim 19 applied for one or more of: treating vascular skin lesions; treating oral lesions; treating oral cancers; treating nail fungus; treating eye disease; treating glaucoma; treating internal lesions; wrinkle removal; skin resurfacing; subcutaneous fat removal; tooth whitening; and removing scars, birthmarks, hyperpigmented regions, hypopigmented regions, or tattoos.

33. A photothermolysis method according to claim 19 wherein the target structure comprises a structure of the eye.

34. A photothermolysis method according to claim 19 wherein the microscope comprises a Raman spectrometer, step (a) comprises visualizing the target with co-registered confocal Raman imaging and at least one of TPF, SHG, and RCM imaging.

35. A microscope according to claim 7 wherein the third detector comprises a Raman spectrometer.

36. A microscope according to claim 35 wherein the portion of the first signal comprises spectra over the wavenumber range of 800-1800 $cm^{-1}$.

37. A microscope according to claim 35 comprising a spectral adapter positioned between the excitation source and the scanner, the portion of the first signal is directed to the spectrometer by a fibre bundle, and wherein the spectral adapter is configured to maintain an end face of the fibre bundle in confocal alignment with a focal point of the excitation beam inside the sample.

38. A microscope according to claim 35 wherein the microscope is operable to simultaneously perform at least two imaging modalities selected from: two-photon fluorescence imaging, reflectance confocal imaging, and two-photon fluorescence spectral measurements.

39. A microscope according to claim 35 wherein the microscope is operable to simultaneously perform at least two of the following imaging modalities: confocal reflectance imaging, two-photon fluorescence imaging, and confocal Raman imaging.

40. A microscope according to claim 39 wherein the at least two imaging modalities are co-registered.

41. A microscope according to claim 35 wherein the microscope is operable to perform both confocal Raman imaging and Raman spectral measurements using the excitation beam.

42. A microscope according to claim 7 wherein the third detector comprises a spectrometer.

43. A method comprising:
(a) visualizing a target structure using a microscope according to claim 35, the target structure comprising blood in a blood vessel;
(b) based on one or more of the signals detected by the microscope determining a level of an analyte in the blood.

44. The method according to claim 43 wherein the analyte comprises glucose.

* * * * *